(12) United States Patent
Bashkirov et al.

(10) Patent No.: US 9,213,107 B2
(45) Date of Patent: Dec. 15, 2015

(54) ION INDUCED IMPACT IONIZATION DETECTOR AND USES THEREOF

(71) Applicant: Loma Linda University Medical Center, Loma Linda, CA (US)

(72) Inventors: Vladimir Bashkirov, Loma Linda, CA (US); Reinhard W. Schulte, Grand Terrace, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

(21) Appl. No.: 14/203,124

(22) Filed: Mar. 10, 2014

(65) Prior Publication Data
US 2014/0191134 A1    Jul. 10, 2014

Related U.S. Application Data

(62) Division of application No. 12/896,671, filed on Oct. 1, 2010, now Pat. No. 8,669,533.

(60) Provisional application No. 61/255,053, filed on Oct. 26, 2009, provisional application No. 61/247,916, filed on Oct. 1, 2009.

(51) Int. Cl.
*G01T 1/185* (2006.01)
*G01T 1/16* (2006.01)
(Continued)

(52) U.S. Cl.
CPC . *G01T 1/16* (2013.01); *G01T 1/185* (2013.01); *G06F 17/5009* (2013.01); *G06F 19/12* (2013.01)

(58) Field of Classification Search
CPC ............. G01T 5/00; G01T 5/16; G01T 5/185; G06F 17/5009; G06F 19/12

USPC .................. 250/374–392; 324/464
See application file for complete search history.

(56) References Cited

U.S. PATENT DOCUMENTS 2,629,831 A    2/1953    Atchley, Jr.
2,737,596 A    3/1956    Haupt et al.
(Continued)

FOREIGN PATENT DOCUMENTS

DE    2 833 800    12/1979
DE    2 755 956    4/1987
(Continued)

OTHER PUBLICATIONS

Abragram: "The Principles of Nuclear Magnetism" at the Clarendon Press, Oxford, 1978, p. 66
(Continued)

*Primary Examiner* — Robert Kim
*Assistant Examiner* — Eliza Osenbaugh-Stewar
(74) *Attorney, Agent, or Firm* — Knobbe, Martens, Olson & Bear LLP

(57) ABSTRACT

Disclosed are systems, devices and methodologies relating to an ion induced impact ionization detector and uses thereof. In certain implementations, the detector can include a dielectric layer having one or more wells. An anode layer defining apertures to accommodate the openings of the wells can be disposed on one side of the dielectric layer, and a cathode such as a solid resistive cathode can be disposed on the other side so as to provide an electric field in each of the wells. Various design parameters such as well dimensions and operating parameters such as pressure and high voltage are disclosed. In certain implementations, such an ion detector can be coupled to a low pressure gas volume to detect ionization products such as positive ions. Such a system can be configured to provide single ion counting capability. Various example applications where the ion detector can be implemented are also disclosed.

4 Claims, 15 Drawing Sheets

(51) Int. Cl.
  *G06F 17/50* (2006.01)
  *G06F 19/12* (2011.01)

(56) References Cited

U.S. PATENT DOCUMENTS

| | | |
|---|---|---|
| 2,876,362 A | 3/1959 | Foderaro |
| 3,175,085 A | 3/1965 | Avery |
| 3,604,931 A | 9/1971 | Kastner et al. |
| 3,621,240 A | 11/1971 | Cohen et al. |
| 3,942,012 A | 3/1976 | Boux |
| 3,955,089 A | 5/1976 | McIntyre et al. |
| 3,975,640 A | 8/1976 | Boux et al. |
| 3,986,026 A | 10/1976 | Martin |
| 4,020,356 A | 4/1977 | Brahme |
| 4,069,457 A | 1/1978 | Martin et al. |
| 4,070,611 A | 1/1978 | Ernst |
| 4,095,114 A | 6/1978 | Taumann |
| 4,112,306 A | 9/1978 | Nunan |
| 4,118,631 A | 10/1978 | Froggatt |
| 4,131,799 A | 12/1978 | Steiber |
| 4,190,772 A | 2/1980 | Dinwiddie et al. |
| 4,198,565 A | 4/1980 | Ono |
| 4,206,355 A | 6/1980 | Boux |
| 4,256,966 A | 3/1981 | Heinz |
| 4,287,425 A | 9/1981 | Elliott, Jr. |
| 4,362,947 A | 12/1982 | Perraudin et al. |
| 4,392,239 A | 7/1983 | Wilkens |
| 4,497,061 A | 1/1985 | Hounsfield |
| 4,517,462 A | 5/1985 | Boyer et al. |
| 4,602,622 A | 7/1986 | Bar et al. |
| 4,624,007 A | 11/1986 | Muranushi |
| 4,686,369 A | 8/1987 | McDaniel et al. |
| 4,764,679 A | 8/1988 | McDaniel et al. |
| 4,789,930 A | 12/1988 | Sones et al. |
| 4,791,934 A | 12/1988 | Brunnett |
| 4,831,254 A | 5/1989 | Jenkins |
| 4,901,339 A | 2/1990 | Heinz et al. |
| 4,907,251 A | 3/1990 | Mork et al. |
| 4,931,653 A | 6/1990 | Hamm et al. |
| 5,012,506 A | 4/1991 | Span et al. |
| 5,014,290 A | 5/1991 | Moore et al. |
| 5,027,818 A | 7/1991 | Bova et al. |
| 5,039,867 A | 8/1991 | Nishihara et al. |
| 5,041,730 A | 8/1991 | Attix |
| 5,048,070 A | 9/1991 | Maehama et al. |
| 5,048,071 A | 9/1991 | Van Steenburg |
| 5,049,147 A | 9/1991 | Danon |
| 5,054,048 A | 10/1991 | Wang |
| 5,054,049 A | 10/1991 | Manabe |
| 5,072,123 A | 12/1991 | Johnsen |
| 5,079,426 A | 1/1992 | Antonuk et al. |
| 5,094,241 A | 3/1992 | Allen |
| 5,107,839 A | 4/1992 | Houdek et al. |
| 5,115,391 A | 5/1992 | Puthenpura et al. |
| 5,117,829 A | 6/1992 | Miller et al. |
| 5,128,543 A | 7/1992 | Reed et al. |
| 5,206,893 A | 4/1993 | Hara |
| 5,230,623 A | 7/1993 | Guthrie et al. |
| 5,240,218 A | 8/1993 | Dye |
| 5,242,455 A | 9/1993 | Skeens et al. |
| 5,256,879 A | 10/1993 | McNulty et al. |
| 5,269,305 A | 12/1993 | Corol |
| 5,278,886 A | 1/1994 | Kobiki et al. |
| 5,281,232 A | 1/1994 | Hamilton et al. |
| 5,297,037 A | 3/1994 | Ifuku |
| 5,347,132 A | 9/1994 | Holzman et al. |
| 5,402,463 A | 3/1995 | Umetani et al. |
| 5,446,548 A | 8/1995 | Gerig et al. |
| 5,485,833 A | 1/1996 | Dietz |
| 5,511,549 A | 4/1996 | Legg et al. |
| 5,538,494 A | 7/1996 | Matsuda |
| 5,553,112 A | 9/1996 | Hardy et al. |
| 5,570,409 A | 10/1996 | Yamaguchi et al. |
| 5,585,642 A | 12/1996 | Britton et al. |
| 5,596,199 A | 1/1997 | McNulty et al. |
| 5,596,619 A | 1/1997 | Carol |
| 5,602,892 A | 2/1997 | Llacer |
| 5,612,783 A | 3/1997 | Hirsh |
| 5,622,170 A | 4/1997 | Schultz |
| 5,625,663 A | 4/1997 | Swerdloff et al. |
| 5,668,371 A | 9/1997 | Deasy et al. |
| 5,676,673 A | 10/1997 | Ferre et al. |
| 5,727,554 A | 3/1998 | Kalend et al. |
| 5,754,623 A | 5/1998 | Seki |
| 5,755,725 A | 5/1998 | Druais |
| 5,768,405 A | 6/1998 | Makram-Ebeid |
| 5,769,779 A | 6/1998 | Alderson |
| 5,792,147 A | 8/1998 | Evans et al. |
| 5,825,845 A | 10/1998 | Blair et al. |
| 5,851,182 A | 12/1998 | Sahadevan |
| 5,878,112 A | 3/1999 | Koertge |
| 5,963,658 A | 10/1999 | Klibanov et al. |
| 5,981,946 A | 11/1999 | Mason |
| 6,052,435 A | 4/2000 | Hernandez-Guerra et al. |
| 6,104,779 A | 8/2000 | Shepherd et al. |
| 6,118,848 A | 9/2000 | Reiffel |
| 6,148,272 A | 11/2000 | Bergstrom et al. |
| 6,178,389 B1 | 1/2001 | Sola et al. |
| 6,180,942 B1 | 1/2001 | Tracy et al. |
| 6,195,409 B1 | 2/2001 | Chang et al. |
| 6,195,578 B1 | 2/2001 | Distler et al. |
| 6,200,025 B1 | 3/2001 | Rich |
| 6,256,591 B1 | 7/2001 | Yoda et al. |
| 6,282,261 B1 | 8/2001 | Mazess et al. |
| 6,307,914 B1 | 10/2001 | Kuneida et al. |
| 6,316,776 B1 | 11/2001 | Hiramoto et al. |
| 6,325,758 B1 | 12/2001 | Carol et al. |
| 6,345,114 B1 | 2/2002 | Mackie et al. |
| 6,365,902 B1 | 4/2002 | Francke et al. |
| 6,373,065 B1 | 4/2002 | Francke et al. |
| 6,385,286 B1 | 5/2002 | Fitchard et al. |
| 6,420,711 B2 | 7/2002 | Tümer |
| 6,437,513 B1 | 8/2002 | Selzer et al. |
| 6,445,766 B1 | 9/2002 | Whitham |
| 6,560,354 B1 | 5/2003 | Maurer, Jr. et al. |
| 6,565,577 B2 | 5/2003 | Cosman |
| 6,650,930 B2 | 11/2003 | Ding |
| 6,694,057 B1 | 2/2004 | Miller et al. |
| 6,731,970 B2 | 5/2004 | Schlossbauer et al. |
| 6,754,299 B2 | 6/2004 | Patch |
| 6,757,355 B1 | 6/2004 | Siochi |
| 6,787,771 B2 | 9/2004 | Bashkirov et al. |
| 6,799,068 B1 | 9/2004 | Hartmann et al. |
| 6,804,548 B2 | 10/2004 | Takahashi et al. |
| 6,810,107 B2 | 10/2004 | Steinberg |
| 6,906,317 B2 | 6/2005 | Bateman et al. |
| 7,081,619 B2 | 7/2006 | Bashkirov et al. |
| 7,142,634 B2 | 11/2006 | Engler et al. |
| 7,207,715 B2 | 4/2007 | Yue |
| 7,247,869 B2 | 7/2007 | Tadokoro et al. |
| 7,268,358 B2 | 9/2007 | Ma et al. |
| 7,398,309 B2 | 7/2008 | Baumann et al. |
| 7,629,598 B2 | 12/2009 | Harada |
| 7,645,996 B2 | 1/2010 | Yang et al. |
| 7,659,528 B2 | 2/2010 | Uematsu |
| 7,695,192 B2 | 4/2010 | Henderson et al. |
| 7,796,730 B2 | 9/2010 | Marash et al. |
| 7,801,270 B2 | 9/2010 | Nord et al. |
| 7,820,989 B2 | 10/2010 | Sommer |
| 7,834,334 B2 | 11/2010 | Grozinger et al. |
| 7,834,336 B2 | 11/2010 | Boeh et al. |
| 7,860,216 B2 | 12/2010 | Jongen et al. |
| 7,934,869 B2 | 5/2011 | Ivanov et al. |
| 7,940,894 B2 | 5/2011 | Balakin |
| 8,045,679 B2 | 10/2011 | Balakin |
| 8,049,176 B1 | 11/2011 | Majewski et al. |
| 8,080,801 B2 | 12/2011 | Safai |
| 8,109,865 B2 | 2/2012 | Jackson |
| 8,111,806 B2 | 2/2012 | Amelia et al. |
| 8,129,699 B2 | 3/2012 | Balakin |
| 8,144,832 B2 | 3/2012 | Balakin |
| 8,223,920 B2 | 7/2012 | Amelia et al. |
| 8,229,072 B2 | 7/2012 | Balakin |
| 8,264,174 B2 | 9/2012 | Liu et al. |

(56) References Cited

U.S. PATENT DOCUMENTS

| | | |
|---|---|---|
| 8,331,531 B2 | 12/2012 | Fahrig et al. |
| 8,334,509 B2 | 12/2012 | Iseki et al. |
| 8,405,050 B2 | 3/2013 | Bert et al. |
| 8,426,824 B2 | 4/2013 | Jongen et al. |
| 8,481,951 B2 | 7/2013 | Jongen et al. |
| 8,487,278 B2 | 7/2013 | Balakin |
| 8,519,365 B2 | 8/2013 | Balakin |
| 8,598,543 B2 | 12/2013 | Balakin |
| 8,601,116 B2 | 12/2013 | Baumann et al. |
| 8,632,448 B1 | 1/2014 | Schulte et al. |
| 8,669,533 B2 | 3/2014 | Bashkirov et al. |
| 8,688,197 B2 | 4/2014 | Balakin |
| 8,750,453 B2 | 6/2014 | Cheng et al. |
| 2001/0016029 A1 | 8/2001 | Tumer |
| 2002/0077545 A1 | 6/2002 | Takahashi et al. |
| 2002/0193685 A1 | 12/2002 | Mate et al. |
| 2003/0007601 A1 | 1/2003 | Jaffray et al. |
| 2003/0095625 A1 | 5/2003 | Steinberg |
| 2003/0146759 A1 | 8/2003 | Bashkirov et al. |
| 2003/0155530 A1 | 8/2003 | Adnani et al. |
| 2004/0042583 A1 | 3/2004 | Wackerle et al. |
| 2004/0158145 A1 | 8/2004 | Ghelmansarai et al. |
| 2005/0020869 A1 | 1/2005 | Hainfeld et al. |
| 2005/0078787 A1 | 4/2005 | Dinten et al. |
| 2005/0090732 A1 | 4/2005 | Ivkov et al. |
| 2005/0109929 A1 | 5/2005 | Bashkirov et al. |
| 2005/0152502 A1 | 7/2005 | Saunders et al. |
| 2005/0259779 A1 | 11/2005 | Abraham-Fuchs et al. |
| 2005/0276861 A1 | 12/2005 | Kipp et al. |
| 2006/0104410 A1 | 5/2006 | Sauer et al. |
| 2006/0166353 A1 | 7/2006 | Alfano et al. |
| 2006/0175529 A1 | 8/2006 | Harmon et al. |
| 2007/0009441 A1 | 1/2007 | Erathodiyil et al. |
| 2007/0031337 A1 | 2/2007 | Schulte |
| 2007/0086560 A1 | 4/2007 | Kia et al. |
| 2007/0122020 A1 | 5/2007 | Claus et al. |
| 2007/0147672 A1 | 6/2007 | Karl et al. |
| 2008/0031414 A1 | 2/2008 | Coppens |
| 2008/0071131 A1 | 3/2008 | Rietzel |
| 2008/0083871 A1 | 4/2008 | Cravens et al. |
| 2008/0142715 A1 | 6/2008 | Yang et al. |
| 2008/0164416 A1 | 7/2008 | Safai |
| 2008/0210878 A1 | 9/2008 | Friedman |
| 2008/0228418 A1 | 9/2008 | Green |
| 2009/0154645 A1 | 6/2009 | Lifshitz et al. |
| 2009/0168960 A1 | 7/2009 | Jongen et al. |
| 2009/0196393 A1 | 8/2009 | Wang et al. |
| 2009/0230315 A1 | 9/2009 | Hunter et al. |
| 2009/0274269 A1 | 11/2009 | Foland |
| 2010/0008468 A1 | 1/2010 | Balakin |
| 2010/0008469 A1 | 1/2010 | Balakin |
| 2010/0027745 A1 | 2/2010 | Balakin |
| 2010/0032564 A1 | 2/2010 | Morris et al. |
| 2010/0054414 A1 | 3/2010 | Herrmann |
| 2010/0301235 A1 | 12/2010 | Bert et al. |
| 2011/0006224 A1 | 1/2011 | Maltz et al. |
| 2011/0049377 A1 | 3/2011 | Morf et al. |
| 2011/0118588 A1 | 5/2011 | Komblau et al. |
| 2011/0182806 A1 | 7/2011 | Schulte et al. |
| 2011/0196223 A1 | 8/2011 | Balakin |
| 2011/0220794 A1 | 9/2011 | Censor et al. |
| 2011/0230754 A1 | 9/2011 | Overweg |
| 2011/0309255 A1 | 12/2011 | Bert et al. |
| 2012/0056109 A1 | 3/2012 | Lomax |
| 2012/0104270 A1 | 5/2012 | Marchand et al. |
| 2012/0136194 A1 | 5/2012 | Zhang et al. |
| 2012/0143051 A1 | 6/2012 | Balakin |
| 2012/0150018 A1 | 6/2012 | Yamaya et al. |
| 2012/0165651 A1 | 6/2012 | Inaniwa et al. |
| 2012/0168630 A1 | 7/2012 | Beddar et al. |
| 2012/0181428 A1 | 7/2012 | Bert et al. |
| 2012/0181442 A1 | 7/2012 | Prieels |
| 2012/0205557 A1 | 8/2012 | Rinecker |
| 2012/0209109 A1 | 8/2012 | Balakin |
| 2013/0015352 A1 | 1/2013 | Karonis |

FOREIGN PATENT DOCUMENTS

| | | |
|---|---|---|
| DE | 10 2005 034 912 | 2/2007 |
| DE | 10 2006 044 139 | 10/2008 |
| DE | 10 2005 056 698 | 11/2008 |
| DE | 10 2009 033 284 | 1/2011 |
| EP | 0 060 771 | 9/1982 |
| EP | 1 538 459 | 6/2005 |
| EP | 1 871 477 | 3/2011 |
| JP | 63-88486 | 4/1988 |
| JP | 01-209077 | 8/1989 |
| JP | 1989-274741 | 10/1989 |
| JP | 03-094736 A | 4/1991 |
| JP | 1992-102465 | 3/1992 |
| JP | 04-339282 | 11/1992 |
| JP | 06-209926 | 8/1994 |
| JP | 07-047079 | 2/1995 |
| WO | WO 87/00682 | 1/1987 |
| WO | WO 98/18523 | 5/1998 |
| WO | WO 00/62096 | 10/2000 |
| WO | WO 02/31535 | 4/2002 |
| WO | WO 03/020196 | 3/2003 |
| WO | WO 2006/104046 | 10/2006 |
| WO | WO 2007/095312 | 8/2007 |
| WO | WO 2007/126782 | 11/2007 |
| WO | WO 2008/067842 | 6/2008 |
| WO | WO 2008/140560 | 11/2008 |
| WO | WO 2008/142695 | 11/2008 |
| WO | WO 2009/018383 | 2/2009 |
| WO | WO 2009/113069 | 9/2009 |
| WO | WO 2009/135202 | 11/2009 |
| WO | WO 2009/142548 | 11/2009 |
| WO | WO 2009/155700 | 12/2009 |
| WO | WO 2010/011676 | 1/2010 |
| WO | WO 2010/015358 | 2/2010 |
| WO | WO 2010/067227 | 6/2010 |
| WO | WO 2010/101489 | 9/2010 |
| WO | WO 2010/109586 | 9/2010 |
| WO | WO 2010/149740 | 12/2010 |
| WO | WO 2011/006732 | 1/2011 |
| WO | WO 2011/100628 | 8/2011 |
| WO | WO 2011/154853 | 12/2011 |
| WO | WO 2011/162851 | 12/2011 |
| WO | WO 2012/024448 | 2/2012 |
| WO | WO 2012/161852 | 11/2012 |

OTHER PUBLICATIONS

Archambeau et al., "Conceptual Design of a Proton Therapy Synchrotron for Loma Linda University Medical Center," Fermi National Accelerator Laboratory, Jun. 1986, in 106 pages.

Archambeau et al., "Design of a Proton Therapy Synchrotron," Fermi National Accelerator Laboratory, Jun. 1986, pp. LL467-LL574 in 54 pages.

Brahme, "Electron Transport Phenomena and Absorbed Dose Distributions in Therapeutic Electron Beams", invited paper, 14th International Congress of Radiology, Rio de Janeiro, Brazil, Oct. 24-29, 1977.

Brahme, et al.: "Optimization of Proton and Heavy Ion Therapy Using an Adaptive Inversion Algorithm", Radiotherapy and Oncology, vol. 15, 1989, pp. 189-197.

Censor, et al., "On Diagonally-Relaxed Orthogonal Projection Methods," SIAM Journal on Scientific Computing, vol. 30, pp. 473-504, (2008).

Chi-square test, 1995, 3 pages. In Dictionary of Economics, Wiley. Retrieved online on Nov. 28, 2012 from <<http://www.credoreference.com/entry/ wileyecon/chi_square_test>>.

Chmelevsky D. et al, "Dispositif Experimental En Vue D'Etudes Dosimetriques Au Niveau Du Nanometre". (1973). pp. 870-885, Procedings of the 4th Symposium on Microdosimetry, XP-002246756.

Cole et al., "Proceedings of a Medical Workshop on Accelerators for Charged-Particle Beam Therapy" by Fermilab. Jan. 24-25, 1985, LL33170-LL33313 in 144 pages.

Delannes, et al.: "The Laitinen Stereoadapter: Application to the fractionated stereotactic irradiation of the brain", Neurochirurgie, 1990, 36:167-175. (in French and with English translation).

(56) References Cited

OTHER PUBLICATIONS

Dixit et al., "Development of Gas Microstrip Detectors for Digital X-Ray Imaging and Radiation Dosimetry", IEEE Instrumentation and Measurement Technology Conference, May 19-21, 1997, vol. 2, pp. 1357-1360.
Doran, et al., "A Complete Distortion Correction for MR Images: I. Gradient Warp Correction.", Phys. Med. Biol., 2005, vol. 50, pp. 1343-1361.
B. Gottschalk, "Double-Scattering System with Optimum Dose Uniformity in Proton Radiotherapy", dated Aug. 1, 1986.
International Search Report and Written Opinion re PCT/US2009/034766, dated Apr. 14, 2009.
International Search Report and Written Opinion of the International Search Authority in PCT/US2011/024644 (WO 2011/100628), dated Aug. 9, 2011.
International Search Report, and Written Opinion, dated Nov. 28, 2012, re PCT/US2012/027911.
Japanese Office Action and Search Report, re JP Application No. 2012-532373, dated Oct. 7, 2014, with English Translation.
Kittle, D. et al., "Technical Note: Rapid prototyping of 3D grid arrays for image guided therapy quality assurance," Am. Assoc. Phys. Med., 2008, vol. 35, Issue 12, pp. 5708-5712.
Krause, et al.: "Adaption of a Synchrotron Control System for Heavy Ion Tumor Therapy," Proceedings of the 1995 International Conference on Accelerator and Large Experimental Physics Control Systems (ICALEPCS1995), Chicago, IL, Oct. 30-Nov. 3, 1995, McC. Crowley-Milling (ed.), P. Lucas (ed.), P. Schoessow (ed.)., Fermi Lab-Co NF-96-069, 1996. S 14-19.
Litt et al. Application of Nonlinear system identification to magnetic resonance imaging and computed tomography. 1995 IEEE-EMBC and CMBRC, Theme 6: Physiological Systems/Modelling and Identification. pp. 1389-1390
Li, et al.: "Sparse Object Reconstruction From a Limited Number of Projections Using the Linear Programming," Nuclear Science Symposium Conference Record, 2002 IEEE, Nov. 16, 2002, vol. 2, pp. 989-993.
Liu et al., "A position-sensitive particle detector with a meander-type delay line", Nuclear Instruments and Methods in Physics Research, vol. A240, 1985, North Holland, Amsterdam, pp. 139-144.
Lombardi et al.: "Report on a position sensitive parallel plate avalanche counter with a distributed constants delay-line-cathode", I.E. E.E. Transactions on Nuclear Science, vol. 33, No. 1, Feb. 1, 1986 New York, US,, pp. 403-406.
McGurk, et al., "Rapid Prototyping Techniques for Anatomical Modelling in Medicine", Ann R Coll Surg Engl, 1997, vol. 79, Issue 3, pp. 169-174.
Metcalfe et al., "Patient Immobilization and Image Guidance," The Physics of Radiotherapy X-Rays and Electrons, Capter 12: 2007, p. 727-764.
Mueller et al., "Reconstruction for proton computed tomography: A practical approach," presented at the 2003 IEEE Nuclear Science Symposium and Medical Imaging Conference, paper M14-342.
Pemler et al., "A detector system for proton radiography on the gantry of the Paul-Scherrer-Institute," Nucl. Instrum. Meth. A, vol. 432, No. 2-3, pp. 483-495, 1999.
Penfold, et al., "A more accurate reconstruction system of matrix for quantitative proton computed tomography," Med. Phys. 36 (10), Oct. 2009, pp. 4511-4518.
Penfold, Image Reconstruction and Monte Carlo Simulations in the Development of Proton Computed Tomography for Applications in Proton Radiation Therapy, Doctor of Philosophy thesis, Centre for Medical Radiation Physics, University of Wollongong, 2010. Retrieved from the Internet http://ro.uow.edu.au/theses/3305; in 202 pages.
Penfold, et al., "Characteristics of Proton CT Images Reconstruction with Filtered Backprojection and Iterative Projection Algorithms," Nuclear Science Symposium Conference Record (NSS/MIC), 2009 IEEE, Nov. 1, 2009, pp. 4176-4180.
Product Overview by BrainLAB Radiotherapy Solutions, 2004, BrainLAB AG, in 6 pages.
Proton Therapy Facility: Engineering Design Report, by Fermi National Accelerator Laboratory, Feb. 1987, LL45441-LL45570, in 130 pages.
Pyarali et al.: "Design and Performance of an Object-Oriented Framework for High-Speed Electronic Medical Imaging," Computing Systems, Usenix Association, Berkeley, CA US, vol. 9, No. 4, 1996, pp. 331-375.
Ramani, et al., "A QA phantom for dynamic stereotactic radiosurgery: quantitative measurements", Med Phys, 1995, vol. 22, Issue 8, pp. 1343-1346.
Sadrozinski et al., Issues in Proton Computed Tomography, Nuclear Instruments and Methods in Physics Research A 511, Jun. 2003, pp. 275-281, in 7 pages.
Schulte, et al.: "Modeling of Radiation Action Based on a Nanodosimetric Event Spectra," 1st International Workshop on Space Radiation Research and 11th Annual NASA Space Radiation Health Investigators' Workship Arona (Italy), May 27-31, 2000. Physica Medica, vol. XVII, Supplement 1, 2001.
Schulte et al., "Conceptual Design of a Proton Computed Tomography System for Applications in Proton Radiation Therapy," IEEE Transactions on Nuclear Science, Jun. 2004, pp. 866-872, vol. 51(3), in 7 pages.
Schulte et al., "Design of a Proton Computed Tomography System for Applications in Proton Radiation Therapy," Nuclear Science Symposium Conference Record, 2003 IEEE, Oct. 25, 2003, vol. 3, pp. 1579-1583.
Schulte et al., Nanoparticle-Enhanced Proton Computed Tomography: A Monte Carlo Simulation Study. Biomedical Imaging: Nano to Macro, 2004, IEEE International Symposium, Apr. 15-18, 2004, pp. 1354-1356 in 3 pages.
Shchemelinin S. et al., "Ionization measurements in small gas samples by single ion counting," (1996), pp. 859-861, Nuclear Instruments and Methods in Physics Research A 368.
Shchemelinin, A. et al., "A Nanodosimeter Based on Single Ion Counting," (1997), pp. 375-378, in Goodhead, et al., "Microdosimetry, An Interdisciplinary Approach".
Shehemelinin S. et al., "First Measurements of Ionisation Clusters on the DNA Scale in a Wall-Less Sensitive Volume," Radiation Protection Dosimetry, (1999), vol. 82, No. 1, pp. 43-50. Nuclear Technology Publishing.
Steckner et al. Computing the modulation transfer function of a magnetic resonance imager. Medical Physics, 1994, vol. 21. pp. 483-489.
Svensson, "Influence of Scattering Foils, Transmission Monitors ad Collimating System on the Absorbed Dose Distribution From 10 to 35 MeV Electron Radiation", Acta Radiol. Ther. Phys. Biol. 19(1971). pp. 443-453.
Takada, et al.: "Proton computed tomography with a 250 MeV pulsed beam," Nucl. Instrum. Meth. A, vol. 273, No. 1, pp. 410-422, 1988.
Wang, et al., "A novel phantom and method for comprehensive 3 dimensional measurement and correction of geometric distortion in magnetic resonance imaging", Magn Reson Imaging, 2004, vol. 22, Issue 4, pp. 529-542.
Xu, et al.: "Towards a unified framework for rapid 3D computed tomography on Commodity GPUs." Manuscript received Oct. 29, 2003. IEEE, 2004, pp. 2757-2759.
Yu, et al., "A phantom study of the geometric accuracy of computed tomographic and magnetic resonance imaging stereotactic localization with the Leksell stereotactic system", Neurosurgery, 2001, vol. 48, Issue 5, pp. 1092-1098.
International Search Report and Written Opinion in PCT/US2010/051221.
Pitts et al. "Effect of Well Diameter upon Microwell Detector Performance" Jun. 2000, IEEE Transactions on Nuclear Science, vol. 47, No. 3, pp. 918-922.

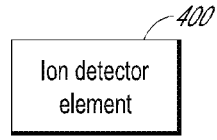
FIG. 21
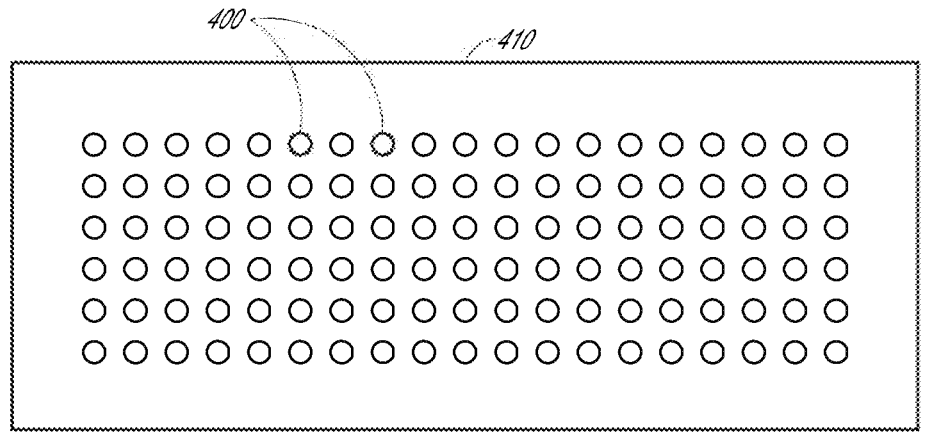
FIG. 22
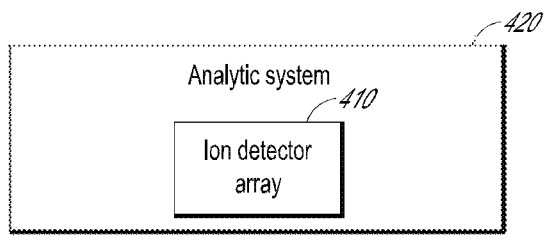
FIG. 23
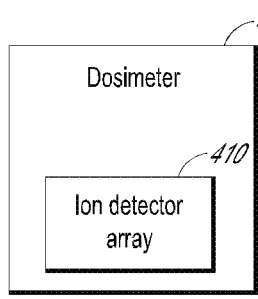 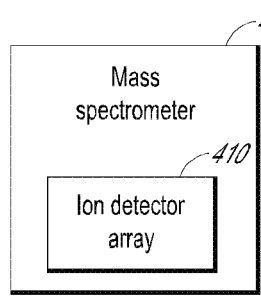 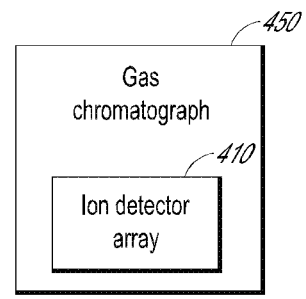
FIG. 24A     FIG. 24B     FIG. 24C

ION INDUCED IMPACT IONIZATION DETECTOR AND USES THEREOF

PRIORITY CLAIM

This application is a divisional of U.S. patent application Ser. No. 12/896,671 (set to issue as U.S. Pat. No. 8,669,533 on Mar. 11, 2014), entitled "ION INDUCED IMPACT IONIZATION DETECTOR AND USES THEREOF," filed Oct. 1, 2010, which claims the benefit of priority under 35 U.S.C. §119(e) of U.S. Provisional Patent Application No. 61/247,916, entitled "ION INDUCED IMPACT IONIZATION DETECTOR AND HIGH-RESOLUTION IONIZING TRACK STRUCTURE IMAGING METHOD," filed Oct. 1, 2009, and U.S. Provisional Patent Application No. 61/255,053, entitled "ION INDUCED IMPACT IONIZATION DETECTOR AND USES THEREOF, filed Oct. 26, 2009, each of which is hereby incorporated herein by reference in its entirety to be considered part of this specification.

BACKGROUND

1. Field

The present disclosure generally relates to the field of ion detectors, and more particularly, to systems and methods for detecting ions so as to allow characterization of interaction of ionizing radiation in matter and for utilization in ion-detection based analytic systems.

2. Description of the Related Art

Some detection apparatus and methods rely on electron detection by detecting current. Although it can be easier to produce and measure electrons, these methods may not be sufficiently sensitive for certain applications.

In certain applications, it may be more desirable to analyze or characterize a sample or an interaction by detecting positive ions. Such positive ions can be generated in a number of ways.

SUMMARY

In certain implementations, the present disclosure relates to an ion induced impact ionization detector that includes an anode having a first side and a second side, and defining a plurality of apertures. The detector further includes a dielectric layer having a first side and second side, where the first side of the dielectric layer is positioned adjacent the first side of anode, and the dielectric layer has a thickness of approximately 1-50 mm. The detector further includes a plurality of wells extending through the dielectric layer, with the plurality of apertures of the anode positioned relative to the plurality of wells so as to define openings between the plurality of wells and the second side of the anode. The detector further includes a cathode positioned adjacent the second side of the dielectric layer forming a bottom of each of the plurality of wells.

In certain embodiments, the thickness is in a range of approximately 1 to 5 mm. In certain embodiments, the thickness is in a range of approximately 2 to 5 mm.

In certain embodiments, the anode includes one or more layers of conductive material. In certain embodiments, the cathode includes a resistive cathode layer.

In certain embodiments, the anode and the cathode are separated by a distance that is substantially the same as the thickness of the dielectric layer.

In certain embodiments, the ion induced impact ionization detector is sensitive to a single ionization event in each of the plurality of wells.

In certain embodiments, the ion induced impact ionization detector further includes a first plurality of readout strips configured in a first orientation and disposed on the first side of the dielectric layer. The detector further includes a second plurality of readout strips configured in a second orientation and disposed on the first plurality of readout strips so as to allow identification of a well that has detected an ion. In certain embodiments, the first and second orientations are substantially perpendicular so as to define X and Y orientations.

In certain embodiments, the ion induced impact ionization detector further includes a third plurality of readout strips configured in a third orientation and disposed on the second plurality of readout strips so as to allow determination of more than one wells that detected ions substantially simultaneously. In certain embodiments, the first, second and third orientations define X, U and V orientations.

In certain embodiments, each of the plurality of wells has a cylindrical shape, and each of the openings defines a circle having a diameter. In certain embodiments, the diameter is selected to be in a range of about one-tenth of the thickness to one thickness. In certain embodiments, the diameter is selected to be in a range of about one-fourth of the thickness to one-third of the thickness.

In certain embodiments, the plurality of wells are arranged in an array so as to define a pitch distance between the edges of two neighboring openings, with the pitch selected so that a ratio between the pitch and the diameter is in a range of about 1 to 5. In certain embodiments, the ratio between the pitch and the diameter is in a range of about 1.1 to 3.

In certain implementations, the present disclosure relates to a detector system that includes an enclosure having a volume of low pressure gas. The system further includes a drift anode disposed within the volume of low pressure gas. The system further includes the ion induced impact ionization detector as summarized above disposed within the volume of low pressure gas so as to define a detection gas volume between the drift anode and the anode of the ion induced impact ionization detector, with the wells having substantially the same low pressure as in the volume of low pressure gas due to the openings. The system further includes an electrical power supply coupled to the drift anode, and the anode and cathode of the ion induced impact ionization detector. The anode of the ion induced impact ionization detector is at a ground potential, the drift anode is at a positive potential relative to the ground, and the cathode is at a negative potential relative to the ground. The positive potential selected to provide a first electric field in the detection gas volume for drifting of a positive ion towards the anode of the ion induced impact ionization detector. The negative potential selected to provide a limited Geiger avalanche in the well where the positive ion drifts into.

In certain embodiments, the low pressure of the gas is in a range of about 1 to 100 Torr. In certain embodiments, the low pressure of the gas is in a range of about 1 to 10 Torr.

In certain embodiments, the negative potential is selected such that an electric field strength within the well is greater than a threshold value associated with breakdown of the gas in the well. In certain embodiments, the negative potential is selected such that the electric field strength within the well is less than a threshold value associated with field emission breakdown at a surface of the well.

In certain embodiments, the negative potential is selected such that an electric field strength within the well puts the gas within the well in a super-tensioned state.

In certain embodiments, one or more dimensions of the well, spacing between the wells, and the negative potential is selected such that an electric field formed within the well is capable of changing as the ion induced avalanche progresses to direct another incoming ion to another nearby well.

In certain implementations, the present disclosure relates to a method of detecting particles. The method includes detecting one or more positive ions using the ion induced impact ionization detector summarized above.

In certain embodiments, the method further includes subjecting the second side of the anode to a gas, and maintaining the environment surrounding the ion induced impact ionization detector at a pressure of less than about 10 Torr.

In certain embodiments, the method further includes applying a negative voltage to the cathode, and maintaining the anode at ground potential such that an avalanche breakdown of the gas in the wells results when a positive ion enters the sell, with the avalanche resulting in a detectable collection of charges.

In certain embodiments, the negative voltage applied is in a range of about 600-900V, and the operating pressure is selected to be less than about 10 Torr. In certain embodiments, the operating pressure is selected to be less than about 2 Torr, and the negative voltage is selected so as to yield a quantity of electric field strength divided by pressure (E/p) has a value of about 2000V/(cm Torr).

In certain implementations, the present disclosure relates to a method for modeling a sample of condensed matter. The method includes identifying ionization clusters responsible for local damage to the condensed matter.

In certain embodiments, the condensed matter is selected from the group consisting of cells, polymers, nanoelectronics and nucleic acid molecules.

In certain embodiments, the method further includes subjecting the condensed matter to ionizing radiation produced by the ion induced impact ionization detector summarized above, where the subjecting step induces an aberration in the condensed matter. In certain embodiments, the method further includes assessing effects of the ionizing radiation on the condensed matter. In certain embodiments, the effects are selected from a DNA double strand break, a central nervous system effect, and cancer induction.

In certain implementations, the present disclosure relates to a method of track ion detection. The method includes imaging a spatial distribution of initial energy deposits in condensed matter by detecting positive ions using the ion induced impact ionization detector summarized above.

In certain embodiments, the method further includes correlating measurements from the imaging step with radiation effects in the condensed matter. In certain embodiments, the ion induced impact ionization detector provides a substantially full topology of the ionization pattern of track segments and resolves single and clustered ionization events along the radiation track over a length in condensed matter.

In certain implementations, the present disclosure relates to a track ion detector having the ion induced impact ionization detector summarized above.

In certain implementations, the present disclosure relates to a mass spectrometer, an ion mobility spectrometer or a gas chromatograph including the ion induced impact ionization detector summarized above.

In certain implementations, the present disclosure relates to a particle detector for detecting the presence and location of a particle. The detector includes a first electrical plate, and a second electrical plate. The first and second electrical plates are biased with respect to each other so as to define an electric field therebetween. The detector further includes an insulating layer interposed between the first electrical plate and the second electrical plate so as to be positioned within the electric field. The insulating layer includes a plurality of wells that extend therethrough, where the wells are spatially distributed so as to receive particles. The wells include opening through which particles can enter. The detector further includes at least one sensor that is positioned with respect to the wells so as to provide signals indicative of the presence of particles within the wells. The electric field, the length of the wells and the atmosphere within the wells are selected so that a charged particle entering the wells results in a limited Geiger avalanche breakdown within the wells thereby resulting in a detectable signal by the sensor indicative of the particle entering the wells.

In certain embodiments, the ratio of the pitch to the well diameter is about 1.1 to 3. In certain embodiments, the wells have a length of approximately 2-5 mm and the atmosphere within the wells is maintained at a pressure of approximately less than 10 Torr, the diameter of the wells is about 0.1-2 mm, and the pitch is about 0.2-5 mm. In certain embodiments, the pressure is less than about 2 Torr, the wells have a length of about 3.2 mm, the diameter of the wells is about 0.8 mm, and the pitch is about 2 mm. In certain embodiments, the detector includes about 1-10,000 wells.

In certain embodiments, the particle detector further includes at least two readout strip layers configured to determine the relative location of detected ions.

In certain implementations, the present disclosure relates to a method for detecting the presence and location of a positive ion. The method includes establishing an electric field in a low pressure gaseous environment to generate ions, where the electric field is sufficient to create a limited Geiger avalanche breakdown. The method further includes detecting a signal produced by the avalanche breakdown.

In certain implementations, the present disclosure relates to a radiation dosimeter that includes a first electrode layer. The dosimeter further includes a second electrode layer having first and second sides, where the first side of the second electrode layer and the first electrode layer define an interaction region occupied by gas molecules at a pressure, and where the second electrode layer defines a plurality of apertures to allow passage of charged particles generated from ionization of the gas molecules by radiation passing through the interaction region. The dosimeter further includes a third electrode layer disposed on the second side of the second electrode layer. The dosimeter further includes an insulating layer interposed between the second electrode layer and the third electrode layer, where the insulating layer defines a plurality of wells open towards the interaction region. The wells are spatially distributed so as to substantially match the plurality of apertures of the second electrode layer and so as to receive the charged particles passing therethrough. The dosimeter further includes a voltage control circuitry configured to provide the first, second, and third electrode layers with different electrical potentials, such that the interaction region is provided with a first electric field that allows drifting of the charged particles towards the second electrode layer without charge multiplication. The wells are provided with a second electric field that results in charge multiplications in wells where the charged particles enter. The dosimeter further includes a detection circuitry in communication with at least one of the second and third electrode layers and configured to detect the charge multiplications in the wells.

In certain embodiments, the charged particles include positive ions generated from the ionization. In certain embodiments, the second electrode layer is electrically connected to an electrical ground. In certain embodiments, the first electrode layer is provided with a positive potential relative to the electrical ground so as to allow drifting of the positive ions towards the second electrode layer. In certain embodiments, the third electrode layer is provided with a negative potential relative to the electrical ground so as to allow acceleration of the positive ions in the wells to induce the charge multiplications.

In certain embodiments, the interaction region is dimensioned and the pressure is selected such that an ionization cross-section in the interaction region is similar to an ionization cross-section of a nano-scale condensed matter object. In certain embodiments, the pressure is selected to be less than approximately 10 Torr so as to allow relatively large expansion of the interaction region dimension to approximate the ionization cross-section of the nano-scale condensed matter object. In certain embodiments, the wells' depth is selected based on the selected pressure and its corresponding range of electric field strength per pressure (E/p) values where the charge multiplication occurs. In certain embodiments, the wells' depth is selected based on probability of the charge multiplication yielding sufficient detectable charge. In certain embodiments, the wells' depth is selected to reduce likelihood of dielectric breakdown of the insulating layer. In certain embodiments, the wells' depth is selected to be about 2 mm or greater. In certain embodiments, the wells' depth is selected to be between about 2 mm and 5 mm.

In certain implementations, the present disclosure relates to a radiation dosimetry method that includes providing a gaseous volume such that radiation passing through the volume has a probability of ionization interaction with gas molecules at a pressure that is similar to a probability of ionization interaction of the radiation with a nano-scale condensed matter object. The method further includes providing a first electric field to the gaseous volume so as to induce drifting of one or more positive ions generated from one or more ionized gas molecules to a first side of the gaseous volume. The first electric field is selected for the gas molecules at the pressure so as to result in the drifting but not in charge multiplication from the one or more positive ions or corresponding electrons. The method further includes detecting the one or more drifting positive ions at the first side so as to characterize the ionization interaction in the gaseous volume. The pressure of the gas molecules and dimension of the gaseous volume traveled by the radiation are selected such that the characterization of the ionization interaction in the gaseous volume approximates the ionization interaction of the radiation with the nano-scale condensed matter object.

In certain implementations, the present disclosure relates to an ion detector element that includes an anode and an insulator layer having a first side and a second side. The first side of the insulator layer is disposed adjacent the anode, and the insulator layer has a thickness in a range of approximately 1-5 mm. The ion detector element further includes a cathode disposed adjacent the second side of the insulator layer. The insulator layer defines a well that extends between the first and second sides of the insulator layer. The well is provided with a gas at a pressure of approximately 1-10 Torr. The anode and cathode provided with an electrical potential difference of approximately 600-900 V.

In certain implementations, the present disclosure relates to a gas chromatograph having one or more of the ion detector elements summarized above.

In certain implementations, the present disclosure relates to an ion mobility spectrometer including one or more of the ion detector elements summarized above.

In certain embodiments, the spectrometer is configured to detect trace amounts of one or more chemicals associated with explosives, drugs, and chemical weapons.

In certain implementations, the present disclosure relates to an ion detector having a plurality of the detector elements summarized above arranged in an array so as to allow spatial determination of ions incident of the detector elements. In certain implementations such an array can be part of a dosimeter. In certain implementations such an array can be part of a mass spectrometer.

For purposes of summarizing the disclosure, certain aspects, advantages and novel features of the inventions have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 21 schematically depicts an ion detector element capable of detecting single ions.

FIG. 22 schematically depicts an array having a number of the detector elements of FIG. 21.

FIG. 23 schematically depicts an analytic system having the detector array of FIG. 22.

FIGS. 24A-24C show non-limiting examples of systems having one or more of the detector element of FIG. 21.

DETAILED DESCRIPTION OF CERTAIN EMBODIMENTS

Figure 1:
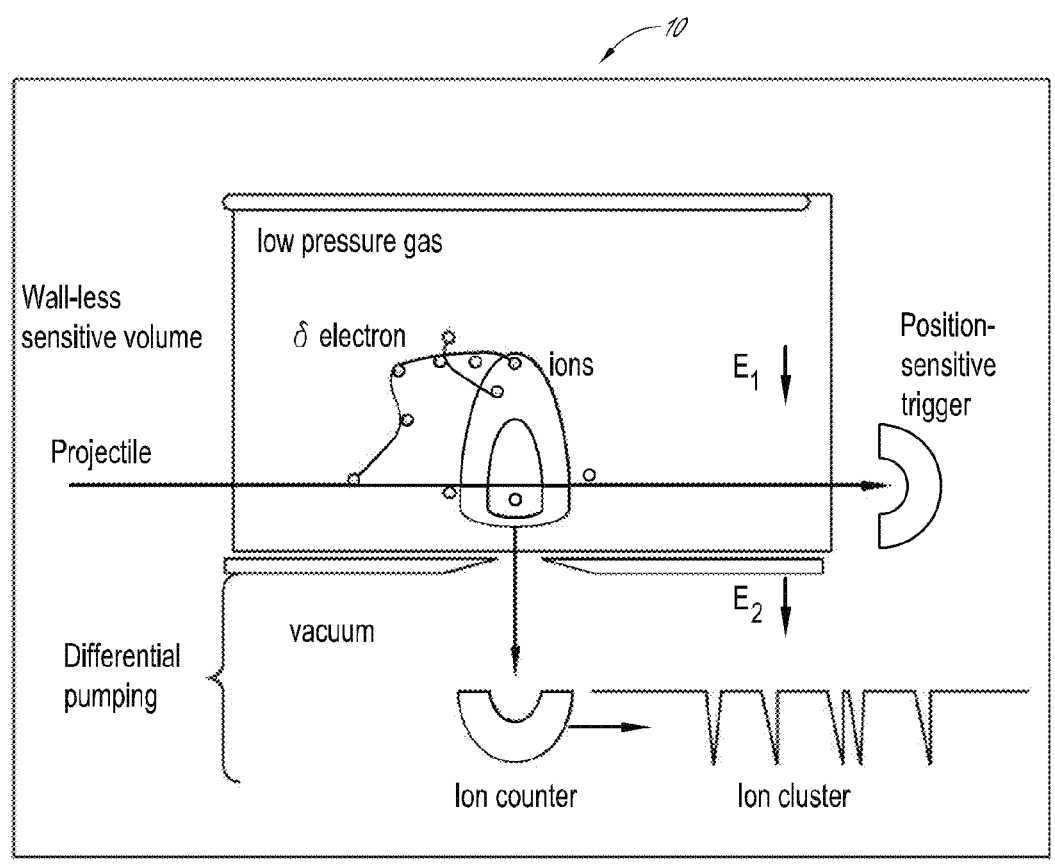
FIG. 1 schematically depicts an example of an ion-counting system where ionization-induced ions are generated in a low-pressure gas volume and extracted into an ion-counter in a high-vacuum environment.

The headings provided herein, if any, are for convenience only and do not necessarily affect the scope or meaning of the claimed invention.

In embodiments described herein, a gas-based detector can address various issues associated with detector designs. As also described herein, scaled dimension (e.g., nanometer scale) equivalent resolution is achievable using one or more features of the present disclosure. Such a resolution capability can be implemented in a number of applications and provide various benefits. For example, patients can benefit because treatment planning of proton and heavy ion radiation therapy can be made more precise by taking the varying biological effectiveness of these particles into account. In another example, society at large can benefit by allowing better definition of radiation exposure limits and thereby protecting its members from unwanted side effects of radiation such as cancer and genetic alterations.

In yet another example, high-resolution imaging of radiation track structure can be achieved using one or more features of the present disclosure. Such a capability can be relevant in many technical fields related to radiation interaction with matter, such as in medicine, physics, radiobiology, and engineering.

Examples for applications or potential applications of track structure imaging in medicine can include optimization of treatment planning for therapy with particles such as protons and heavy ions, and evaluation of space radiation for cancer risk estimates. Applications in other fields can include solar neutrino studies, dark matter search, x-ray polarimetry in astrophysics, radiation protection, nuclear waste management, radiation therapy planning with charged particles, manned space missions and damage to micro- and nano-electronic elements in intense radiation fields in accelerator and outer space environments. In certain implementations of the present disclosure, nanometer-equivalent resolution capability can be applied to some or all of the foregoing example applications.

An important field that can benefit from precise track-imaging devices is the study of radiation damage to cells and DNA. Current devices and methodologies for track-imaging, however, are generally not suitable for track-structure studies on the DNA-to-chromosome scales. In certain situations, study of interactions at such nanometer-scales can be facilitated by detectors and devices that are sometimes referred to as nanodosimeters.

In certain implementations of the present disclosure, a device (e.g., a nanodosimeter) can be configured to detect positive ions which are induced by particle radiation in a low-pressure gas (e.g., propane of about 1 Torr). The use of the low gas pressure allows scaling down a millimeter-size gas volume from which ions are collected to an equivalent unit density volume of nanometer size. In this particular example, the scaling is by a factor of about $10^{-6}$. The nanodosimeter thus can simulate a short segment of DNA of about 20 nm in length and 2-4 nm in diameter.

In certain implementations, the foregoing example nanodosimeter can be configured to a frequency of ion clusters of different sizes formed in such a volume. Such information can be of interest for biomedical applications due to, for example, a hypothesis that large clusters, despite being relatively rare, are mainly responsible for irreparable DNA damage in a living cell.

There are a number of ways for detecting ionization products such as positive ions. For example, FIG. 1 schematically depicts an embodiment of an ion-counting nanodosimeter 10. Ionization-induced ions are shown to be deposited in a sensitive volume such as a volume of low-pressure gas (e.g., 1 Torr propane). The ions formed in such a volume, representing, for example, a DNA segment, are shown to be extracted into a high-vacuum ion-counter, where they are multiplied and individually detected and counted. The number of ions formed in the sensitive volume can be proportional to the deposited energy; and the detectable time delays along a pulse trail can provide information about the interaction location along the sensitive volume (DNA) axis.

In certain embodiments, information obtained from such ion measurements can be used to characterize different types of radiation at various energies. Such characterization of radiation and its representative interaction with matter (e.g., nano-scale condensed matter) can be used, for example, to refine simulation models.

Figure 2A:
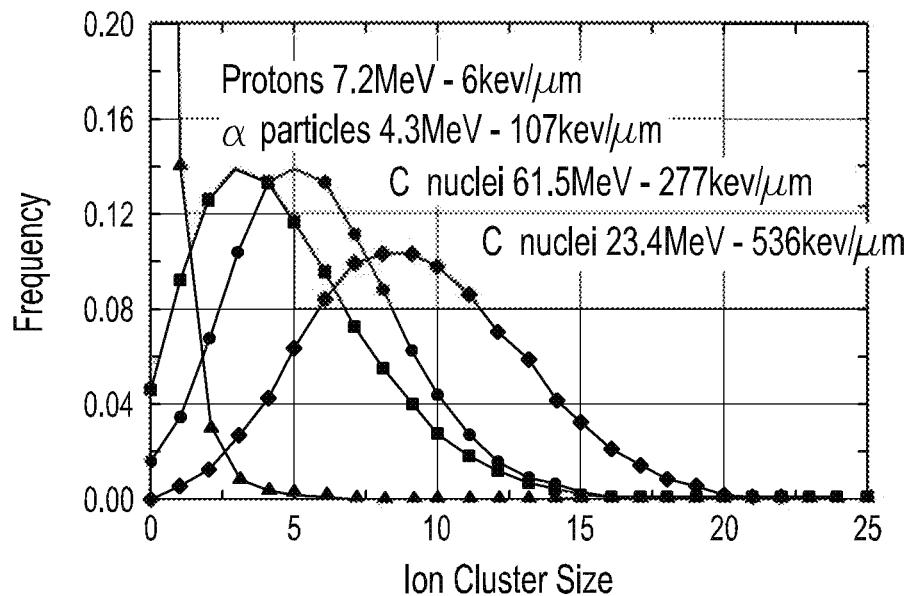
FIG. 2A show distributions of sizes of ion-clusters that can be induced by protons, alpha-particles and carbon ions, in a gas volume of propane at about 1 Torr.
Figure 2B:
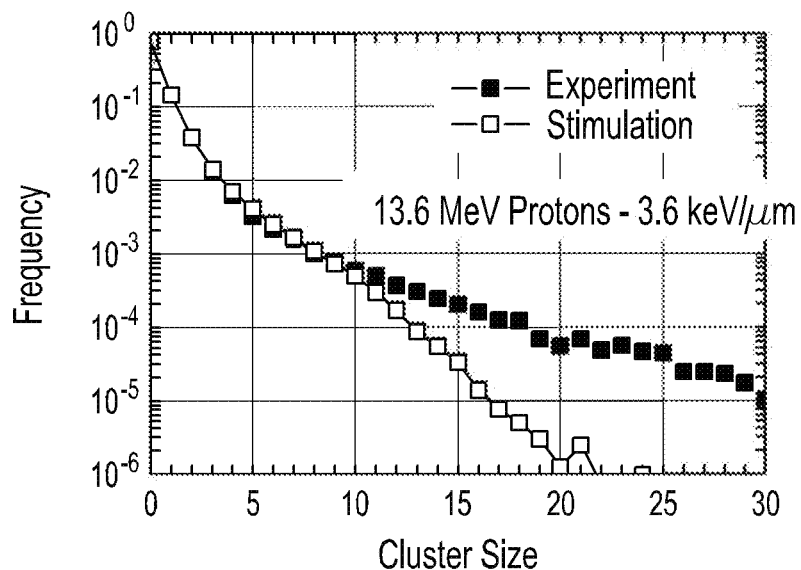
FIG. 2B shows a comparison of Monte-Carlo model simulations with the experimental data over 3.5 orders of magnitude.

For example, FIG. 2A shows various ion-cluster size distributions induced by protons, alpha particles and carbon ions, in the example sensitive volume of the nanodosimeter described in reference to FIG. 1 (operated at approximately 1 Torr of propane gas). FIG. 2B shows a comparison of Monte-Carlo model simulations, where there is substantial agreement with experimental data over 3.5 orders of magnitude, as well as divergence in other regions. Such differences can be addressed in the model appropriately.

In the example of FIGS. 1 and 2, counting of ions is performed at a selected location with respect to the sensitive volume; and spatial information about the ionization events are obtained from the ion pulse train.

In accordance with certain implementations of the present disclosure, an ion induced impact ionization detector described herein can permit substantially full track structure imaging. In certain embodiments, the ion induced impact ionization detector described herein can have a sensitive volume with a simple geometrical shape (e.g., a cylinder, a sphere or a box). In certain implementations, the ion induced impact ionization detector described herein may be used to measure a correlation of clustered ionization events over chromosomal-equivalent dimensions.

In certain embodiments, there is no significant pressure difference between the sensitive volume and the ion counter; thus obviating a double differential pumping system (e.g., a system having two turbomolecular pumps) generally associated with the example device of FIG. 1. Therefore, the ion induced impact ionization detector described herein can be relatively compact, mobile and inexpensive. The lack of a significant pressure gradient can also minimize the distortion of ionization clusters as the clusters move through the gradient.

In certain implementations, one or more features of the present disclosure can be related to nanodosimetry track-structure imaging methods that can provide a substantially full topology of the ionization pattern of track segments and efficiently resolve single and clustered ionization events along the radiation track over a length in condensed matter.

Figure 3:
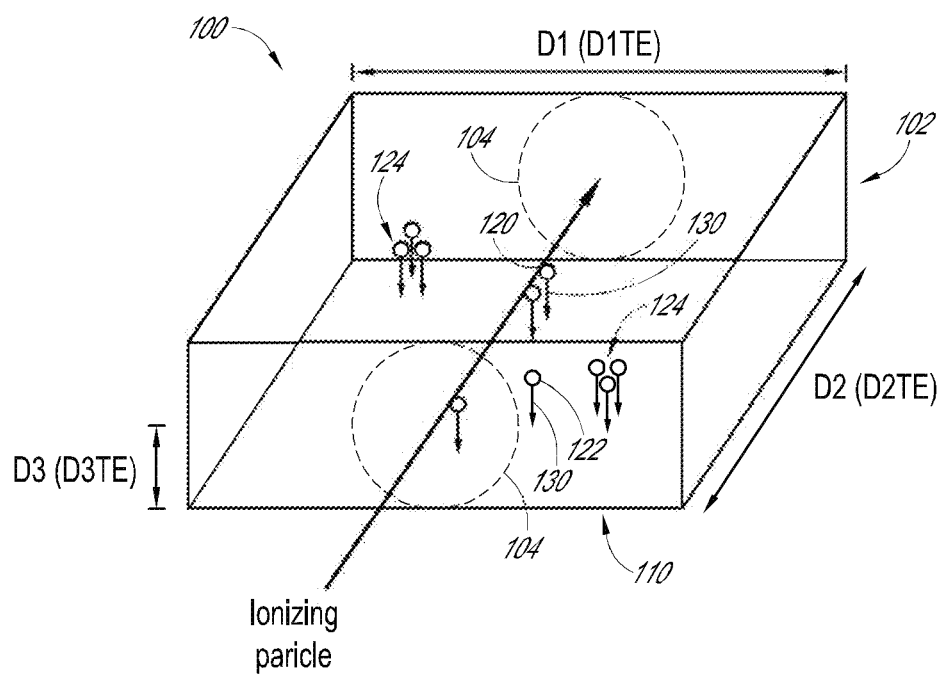
FIG. 3 shows that in certain implementations, a two-dimensional array of ion detectors can be configured to detect ions such as those resulting from ionization in a gas volume, where the ion detector array can be operated in a similar gas pressure environments as that of the gas volume.

In certain implementations, a low-pressure (e.g., ~1 Torr) gaseous detector can be provided. FIG. 3 schematically depicts a gaseous detector 100 having a volume (D1×D2×2D3 in lab frame, and D1TE×D2TE×2D3TE in tissue-equivalent representation) of gas (102) where ionizations are shown to be induced along a given track segment of an ionizing particle. For example, each of D1TE and D2TE can have a TE dimension of about 100 nm. Examples of D3TE dimensions are discussed below.

Primary ionizations are indicated as 120; secondaries as 122. Cluster formations are indicated as 124. The ionization products are depicted as drifting (arrows 130) towards a detection plane 110. In certain embodiments, the detection plane 110 can include a two-dimensional array of positive-ion detectors as described herein.

The detection plane 110 shown in FIG. 3 can be positioned on one side of the gas volume 102. In certain embodiments, the gas volume 102 and/or the positioning of the detection plane 110 can be selected so as to keep the drift distances of the induced ions to the detection plane as 110 small as possible. For example, according to a calculated estimate, a tissue-equivalent (TE) cylinder (depicted by circles 104 at the entrance and exit of the gas volume) of about 16 to 40 nm radius (D3TE in TE representation) centered about the primary track contains about 95% of the ionizations (primaries 120 and secondaries 122) induced by 1 to 100 MeV protons, respectively. In propane of 1 Torr, this corresponds to radius range of about 6 to 15 mm (D3 in the lab frame).

Interaction of radiation with the detector gas can lead to a trail of molecular excitations and ionizations. The latter, in the form of electron-ion pairs, can be utilized in micro- and nanodosimetry for the measurement of the deposited energy as well.

In certain implementations, various detector parameters such as the detector size, including the drift length in the laboratory frame, $l_{LAB}$, and the cell size can be based on the gas pressure. Generally, the higher the pressure, the cell size and the overall detector dimension can be smaller. For example, at 1 Torr of propane (with a scale conversion of 1 mm gas being equivalent to about 2.6 nm TE), the vertical size (representative of an upper limit in drift length) of the detector can be about 6 and 15 mm for 1 and 100 MeV protons, respectively. In some embodiments, in order to image tracks of about 1 µm length, the imaging plane of the detector can have a size of approximately 400×400 mm². The cell size in such a detector can be about 0.2 mm² (approximately 0.5 nm² TE cells).

Figure 4A:
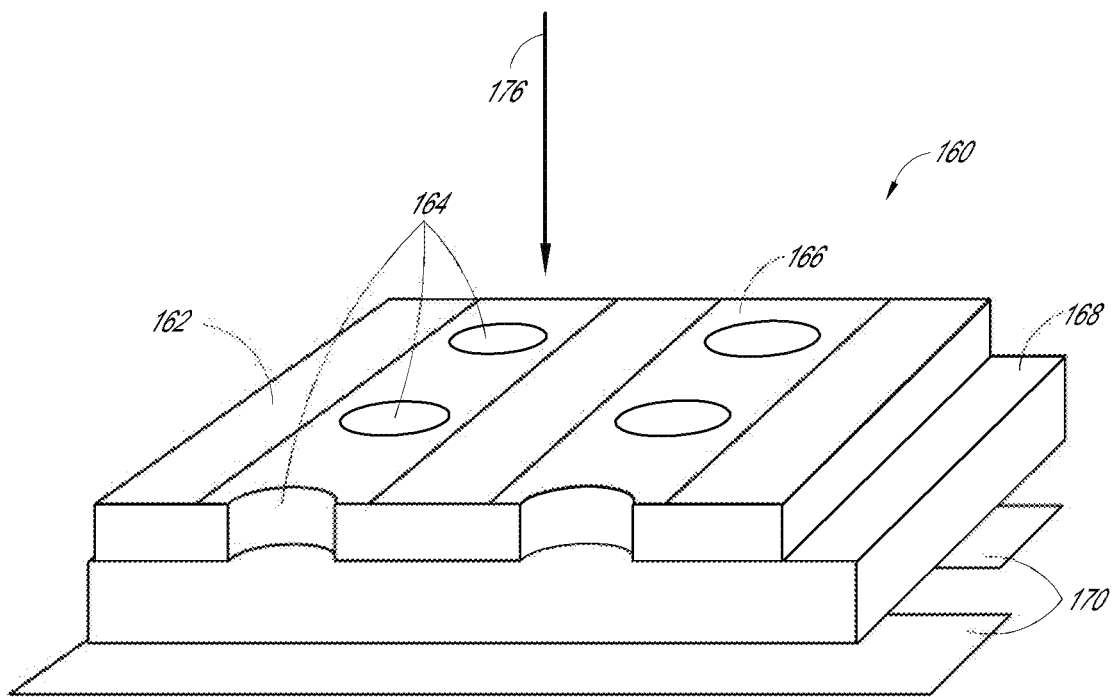
FIG. 4A depicts a portion of a two-dimensional ion detector that can be used for a number of purposes including imaging, where the detector can include an array of wells formed in a dielectric layer.
Figure 4B:
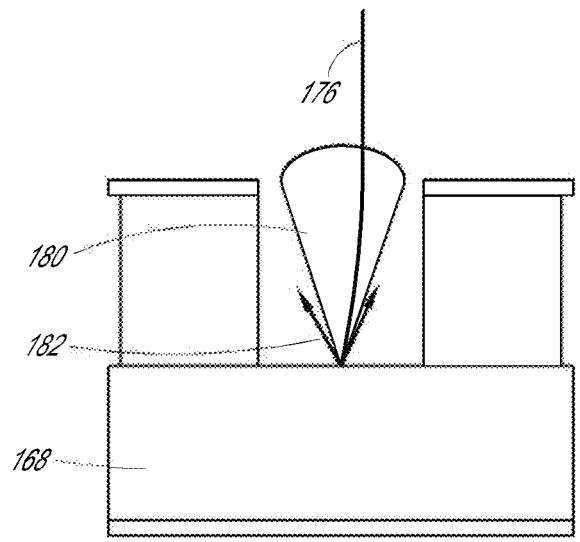
FIG. 4B shows a more detailed view of one of the wells of the detector in FIG. 4A.

FIG. 4A shows a portion 160 of an array of detection cells 154. FIG. 4B shows an expanded view of one of the detection cells of FIG. 4A.

In the example shown, a relatively large number of independent well-based gaseous detectors 164 can be provided. In certain embodiments, the detectors 164 can operate in a limited Geiger mode (fired/not fired).

The use of a relatively large number of individual detecting cells can provide high detection efficiency for single ions, despite the relatively large dead time that may exist in individual cells operating in Geiger mode. Due to the diffusion of the ions, at low gas pressures, even ions originating from the same deposition point will likely be registered in different cells. Hence, the effective counting efficiency of some embodiments can be very high.

In certain implementations, each gaseous detector 164 can be configured to multiply an ion 176 incident therein. Individual positive ions, originating from radiation-induced primary and secondary (delta-electrons) ionizations along the track of a charged particle, may drift under an electric field across-the interaction volume to the ion-multiplier 164. In some embodiments, the ion-multiplier 164 can have a hole-type detector structure such as the ones shown in FIGS. 4A and 4B.

In certain embodiments, the ion-multiplier 164 can be configured to have some similarities with devices such as what is sometimes referred to as a micro-well detector (MWD). Unlike the MWD device, however, certain embodiments of the ion-multiplier 164 can operate in a limited Geiger mode under reversed polarity.

More particularly, a typical MWD device is designed to be triggered by an electron entering the micro-well. Accordingly, an anode is typically placed at the bottom of the micro-well, and a cathode at the entrance surface. Thus, electrons resulting from the multiplication process in the micro-well are thus accelerated to the anode, and charge signals can be collected therefrom.

As described herein, certain embodiments of the present disclosure can include an arrangement of electrodes that are substantially reversed from typical MWD devices. In such a reverse-polarity arrangement, a cathode can be positioned at or near the bottom of a well, and an anode (relative to the cathode) at or near the entrance surface. Various non-limiting examples of such a configuration—by itself or in combination with a detection gas volume—are described herein in greater detail.

It is noted that some embodiments of an MWD device can include a densely perforated holes formed on relatively thin insulator layer (e.g., an approximately 50 µm-thick Kapton layer with a thin metal clad on each of both faces. Such an insulator layer can include holes (e.g., 50 µm diameter). In such a configuration, and with the foregoing MWD polarity of electrodes, radiation-induced electrons can be focused into the wells and be multiplied therein.

In certain embodiments, the detector array 160 can be much thicker than the foregoing MWD example. The insulator layer (162) can have a thickness in a range of about 1-5 mm, and its upper surface can be provided with thin metal strips as readout strips 166. Each of the holes can have a diameter in a range of about 0.5-1 mm; and the holes can be spaced by a distance in a range of about 200-1000 µM. In some embodiments, to obtain a Geiger mode of operation, a highly resistive electrode layer (168) can replace the conductive layer at the bottom of the well.

In certain embodiments, the focusing of an ion into the well 164 and the charge multiplication process within the well can be controlled by an electric field across the well. Such an electric field can be provided by applying a negative voltage to the lower resistive electrode 168. The upper electrode 166 can be formed of strips common to each row of holes, and be kept at a ground potential.

It is noted that a well-based detector having a relatively small separation distance between the electrodes can be provided with an operating voltage difference between the electrodes. Approximating the arrangement of such electrodes as parallel plates, such a voltage difference (V) can be represented by the electric field strength (E) times the separation distance (d). To maintain the same electric field strength within the well (so as to provide a similar detection process) for a relative thicker dielectric configuration, the corresponding increase in separation distance (d) makes it necessary to increase the voltage (in a linear manner). Utilizing such a relatively thick detectors in certain operating conditions can result in a large and potentially harmful voltage difference.

An ion entering the cell 164 can undergo collisions with gas molecules and/or positive-ion impact ionizations of the gas to yield an electron avalanche 180. In addition, the ion can collide with the walls or bottom electrode of the cell, resulting in secondary electron emission (182 in FIG. 4B). Cross sections for such ionizing ion-gas collisions can depend on the type of gas, gas pressure and on the electric field strength associated with the cell. Available data for positive ion impact ionizations are relatively scarce; thus, available data for $O_2$-$N_2$ collisions (J. B. Hasted, Physics of Atomic Collisions, London Butterworths, 1964) were used to obtain some rough estimations herein.

Figure 5:
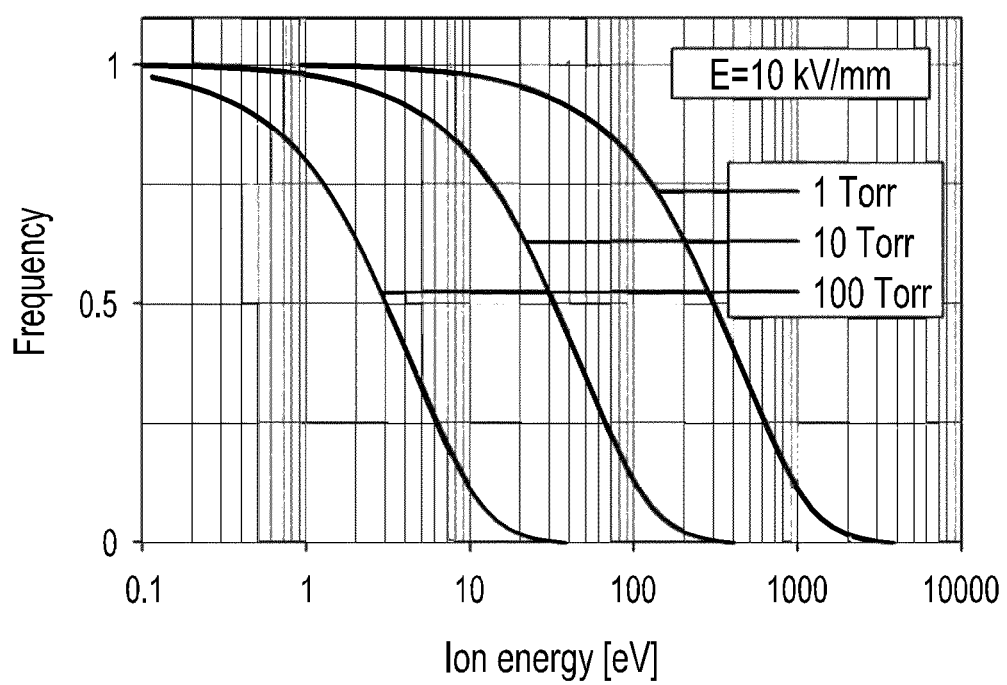
FIG. 5 shows examples of calculated energy distributions of radiation induced ions that are drifting in propane across a well under a field of approximately 1000V per 0.1 mm.

For example, referring to FIG. 5, energy distributions of ions in a 0.1 mm thick well were obtained with an ion transport model configured for calculations for embodiments of the ion counting nanodosimeter described herein.

The resulting estimated probabilities for gas ionization by positive ions are presented in Table 1. The values listed in Table 1 are approximate values. The listed probability for each gas pressure is a probability for at least one gas ionization in a well of approximately 0.1 mm depth under an electric field strength of approximately 1,000V/0.1 mm.

TABLE 1

| Pressure, Torr | Mean energy of ions, eV | Probability of at least one ionization |
| --- | --- | --- |
| 1 | 470 | 15% |
| 10 | 50 | 2.5% |
| 100 | 5 | 0.25% |

The values presented in Table 1 assume that ionizations are only caused by ion-molecule collisions. Charge-exchange collisions, resulting in fast neutral molecules, can also induce ionizations but with far lower probabilities. These rough estimations show that collision ionizations in the gas phase have a very low probability to create secondary electrons (at best 0.15 at 1 Torr), and will, therefore, not provide a desired efficiency for detecting ions. Therefore, micro-pattern detector thickness of about 0.1 mm is generally too small for providing high efficiency of single positive ion registration. Accordingly, a thicker (e.g., a few mm) detector structures can be provided to yield high probability (e.g., close to 100% probability) of ion impact ionization as the ion travels in the cell.

The ionization probability can also be increased by providing higher electric field strength. However, such a higher electric field can result in field emission breakdown that can permanently damage the detector structure.

In the limited Geiger mode, the electrons can initiate a substantially unrestricted avalanche in the cell hole; and such an avalanche can develop due to ionizing collisions of secondary electrons with the gas molecules. The process, once started, can go on until substantially all gas in the hole is ionized. A discharge can develop, unless the electric field is restricted by space charge effects and/or by an external device or circuit (e.g., a resistor in the high-voltage bias chain), as in a Geiger counter. In certain situations, the discharge can be stopped when the voltage drops due to the high volume resistivity of the cell's bottom negative electrode.

In the limited Geiger mode, each cell can operate as an independent Geiger micro counter, and an output signal can determined by the charge accumulated in the cell's capacitor. Such a charge can be represented as $Q_{CELL}=C_{CELL}V$, where $C_{CELL}$ is the capacitance and V is the operating voltage across the cell. Depending on the cell size, $C_{CELL}$ can of the order of tens of fF (femtofarad); thus for V in a range of about 500 to 1000V, $Q_{CELL}$ value in the tens of pC (picocoulomb) range can be expected. In certain implementations, such a charge output can be read out and processed.

Recovery time of the cell can depend on the charge collection time and recharging time; and the former is expected to be in a sub-µs to µs range. In embodiments where the gas pressure is low (e.g., about 1 Torr), such a recovery time generally should not affect the ion detection efficiency; and in particular, at relatively low ionization densities. In such ionization densities, more than one ion entering the same cell is quite rare. Further, ions will likely arrive spaced in time due to their relatively low drift velocities (e.g. about 0.05 cm/µs in 1 Torr propane, at 100 V/(cm Torr)).

Figure 6A:
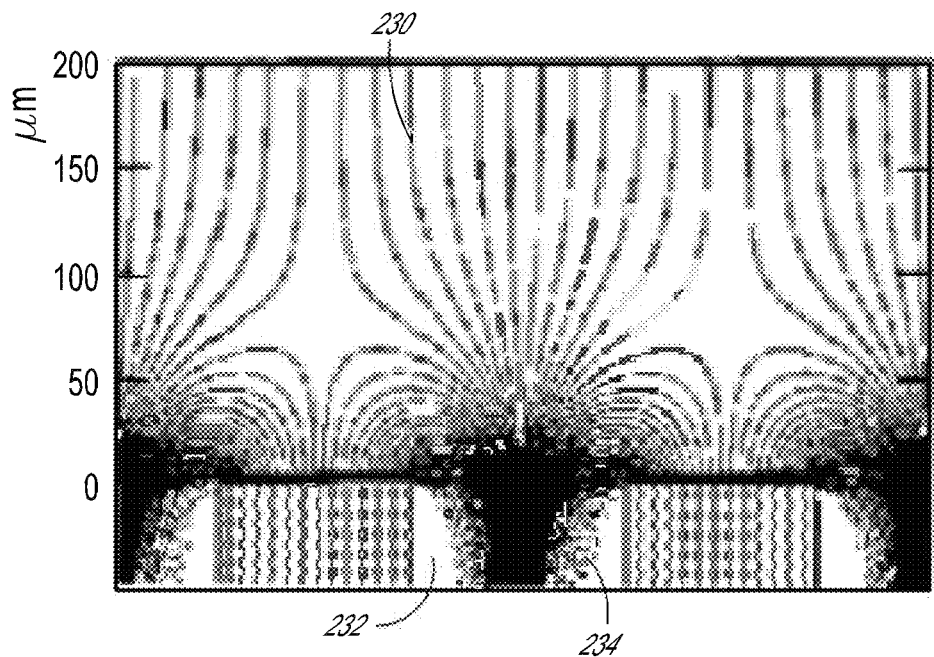
FIGS. 6A and 6B show example electric field lines in a well during and close to termination of a limited-Geiger avalanche triggered by a positive ion.

A detector operating as a micro-Geiger cell structure 232 can include a feature where the electric field 230 configuration can change during the discharge development within a hole. It can be a dynamic process that can be explained on the basis of the electron trajectories shown in FIGS. 6A and 6B before, during, and close to the end of the discharge associated with electrons 234. As one can see, majority of secondary electrons 234 are collected on the strips in an initial stage of the discharge (FIG. 6A), because they are produced in the vicinity to the strips.

Figure 6B:
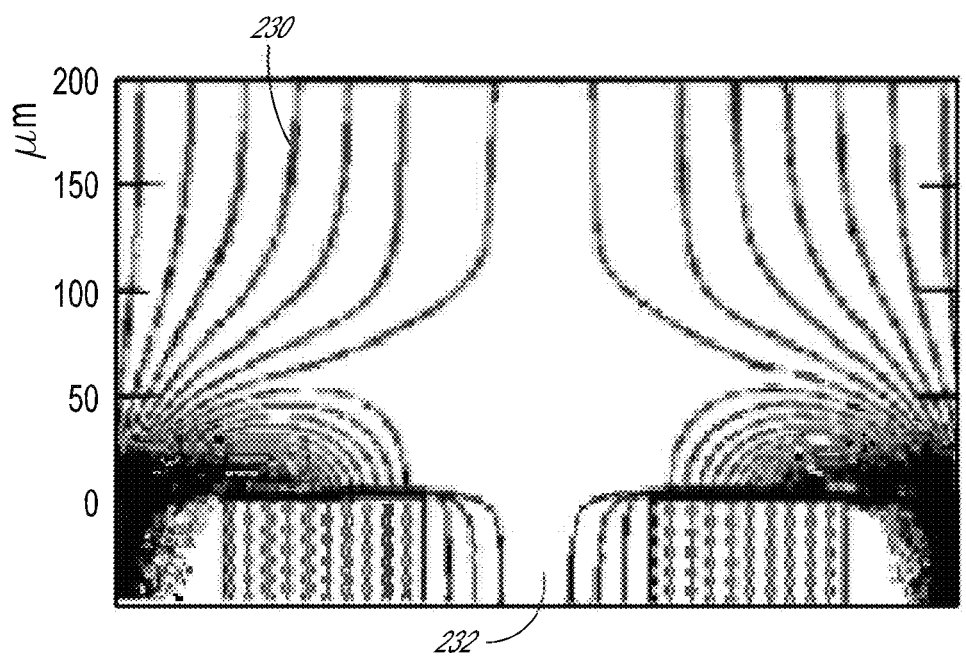

The cell field can drop due to the positive charge of the ions screening the charge on the resistive electrode at the bottom of the well. The field of non-active neighboring cells can expand to the vacant region to trap remaining electrons which otherwise would drift upwards to the ionization volume and deflecting any subsequently arriving ion into a nearby vacant cell. The remaining electrons can be slowly collected in the reduced field configuration, again by the strips (FIG. 6B).

In certain situations, some electrons can escape the trap or hit the cell's sidewalls. Such a dynamic process and estimating effects such as electron escape and possible wall up-charging can be difficult to simulate.

A detected signal can be induced by electrons extracted from the cell and collected by grounded electrode strips. In the Geiger mode, such readout strips can be deposited on the cell's anode. Additional pick-up strips (e.g., 170 in FIG. 4A) on the lower side of the negative electrode can provide a second coordinate. Alternatively, a pixelized 2D readout circuit can be directly coupled to the bottom of the device and measure avalanche-induced signals. With such a readout system, the detector can provide a 3D image of the track, where a strip or pad readout circuit can provide the 2D position of the detected ion, and the pulse timing signal can provide the third coordinate.

In certain embodiments, an optical readout technique can be implemented. Such a configuration can include recording avalanche-induced photons with a sensor such as an intensified CCD camera system. The CCD camera can provide a 2D image of the track, and the third coordinate can be provided by simultaneously recording the avalanche-light flashes with photomultiplier tubes. In the example detector configuration shown in FIG. 4A, an optical readout component 174 can include such a sensor (e.g., CCD camera). Further, an optical element 172 such as a lens can facilitate delivery of light signals to such an optical readout component 174.

Figure 7:
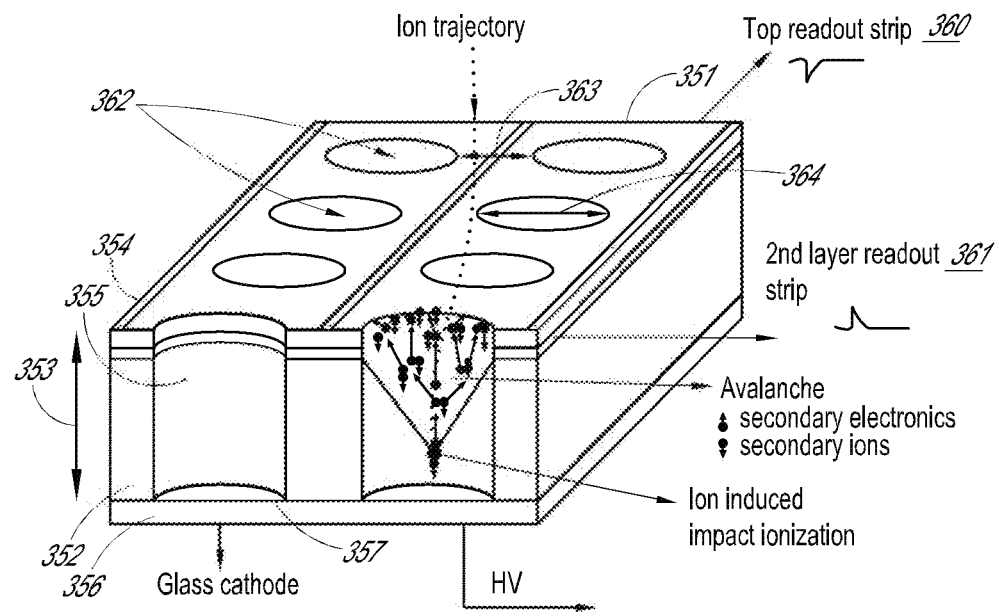
FIG. 7 shows a portion of a detector apparatus having a number of wells configured to facilitate ion induced impact ionization.

FIG. 7 depicts an example ion detector 351. It will be understood that such a depiction is not necessarily to scale. The detector 351 can include a number of cells formed on a dielectric layer or an insulating layer 352. The dielectric layer 352 can include but not limited to insulator materials such as ceramic, silicon dioxide, oxidized surface, porcelain or the like with negligible electrical conductivity. In certain embodiments, a printed circuit board insulator (e.g., FR4) can be used as the insulating layer 352. In certain embodiments, one side of the dielectric layer 352 is adjacent an anode layer 354, and the other side is adjacent a cathode layer 356 (e.g., a glass cathode layer). In certain embodiments, the dielectric layer 352 can be directly adjacent to the anode 354 and/or cathode layer 356, so that there is no intervening layer.

In some embodiments, a distance between the two electrical plates or electrodes 354, 356 defining an inter-electrode gap distance can be similar to or approximately the same as the thickness (353) of the dielectric layer 352. In certain embodiments, such an inter-electrode gap distance can be in a range of about 1 mm to few cm (e.g., 5 cm). In certain embodiments, the gap distance can be in a range of about 1 mm to 5 mm. In certain embodiments, the gap distance can be in a range of about 2 mm to 5 mm. In the example detector described in reference to FIGS. 7 and 8, the gap distance can be approximately 3.2 mm. In certain embodiments, the gap distance between the electrodes 354, 356 may or may not be the same as the thickness of the dielectric layer 352.

In certain implementations, an increase in operating gas pressure can be accommodated with a decrease in the inter-electrode gap distance. Thus, for example, for a gas pressure of about 10 Torr, a gap distance in a range of about 1-2 mm may be appropriate. For a lower gas pressure of about 1 Torr, a gap distance of about 5 mm may be appropriate. In the example detector described in reference to FIG. 8 where the inter-electrode gap distance is about 3.2 mm (e.g., a thickness of a PCB), a gas pressure of about 2 Torr can be appropriate for ion measurements.

In certain implementations, the inter-electrode gap distance and/or the gas pressure can be adjusted for different types of gases.

In certain embodiments, the anode layer 354 may be formed from conductive materials such as metal (e.g., silver or copper). The anode layer 354 may be further coated with materials such as inert metal (e.g., gold or palladium). The anode layer 354 may include openings that substantially align with the openings of the wells 355 in the dielectric layer 352.

In certain embodiments, the anode layer 354 can include strips common to each row of wells 354. In certain embodiments, the anode layer 354 can define openings corresponding to well-openings but otherwise substantially cover one side of the dielectric layer 352. In certain embodiments, the anode layer 354 can be substantially continuous or discontinuous, and can cover at least a portion of the dielectric layer 352.

In certain implementations, the cathode layer 356 can include an electrode on one side of the dielectric layer 352 opposite from the side where the anode layer 354 is positioned. In certain embodiments, the cathode layer 356 can include a resistive cathode that can be formed from optically transparent or semitransparent materials such as conductive glass if optical detector readout is desired or implemented. In certain embodiments, the resistive cathode can include resistive Kapton, conductive ceramic, or composite material such as ruthenium resistive paste fired on appropriate substrate (e.g., silica, glass).

In certain embodiments, the resistive cathode 356 can be a layer which forms the bottom (357) of the well 355 in the dielectric layer 352. The resistive cathode 356 may or may not be directly adjacent the dielectric layer 352. In certain embodiments, there is no intervening layer such as metal between the resistive cathode 356 and the dielectric layer 352.

The dielectric layer 352 can define wells 355 having openings 362 formed on the side adjacent the anode layer 354. The anode layer 354 can also define similarly dimensioned and positioned opening. In certain implementations, such openings can be formed by techniques such as reactive ion etching, printed circuit board (PCB) technology, or other appropriate methods. In the example shown in FIG. 8, the wells 355 extend to the upper surface of the cathode 356 so that the cathode 356 defines a floor 357 of each well 355.

Figure 8:
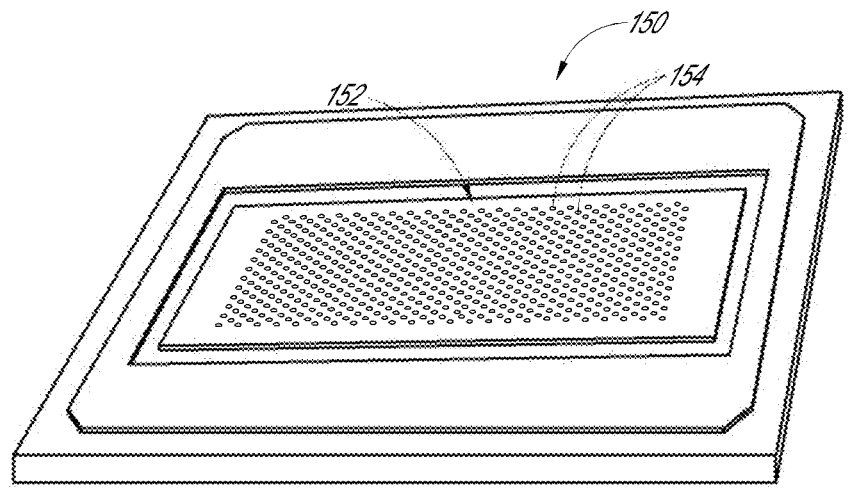
FIG. 8 shows that in certain embodiments, the detector apparatus of FIG. 7 can be fabricated on a printed circuit board (PCB).

For the purpose of description of FIG. 8, the wells are sometimes referred to as cells.

In certain embodiments, the openings 362 allow the wells 355 to be in communication with a gas volume (not shown) above the detector 351. Thus, the wells 355 can be occupied by the same gas at substantially the same pressure as that of the gas volume.

In the particular example 351 described in reference to FIG. 8, the dielectric layer 352 has a thickness (353) that is about 3.2 mm thick. Each of the wells 355 is cylindrically shaped, and has a diameter (364) of about 0.8 mm. The wells 355 are arranged in an array with a pitch (363) of about 1 mm.

In certain implementations, the dielectric layer thickness 353 can be less than or equal to the gap distance between the electrodes 354, 356. Accordingly, in certain embodiments, the thickness 353 can be in a range of about 1 mm to few cm (e.g., 5 cm). In certain embodiments, the thickness 353 can be in a range of about 1 mm to 5 mm. In certain embodiments, the thickness 353 can be in a range of about 2 mm to 5 mm. In the example detector described in reference to FIG. 8, the thickness 353 can be approximately 3.2 mm.

In certain implementations, wells described herein can include a plurality of holes 355 in the dielectric layer 352. The holes may have a relatively simple geometric shape such as cylindrical or rectangular shape. In certain embodiments, the well opening 362 or the cross sections of the wells 355 can be substantially round.

In certain implementations, diameter 364 of each hole can be in a range of about 0.1-2 mm, 0.5-1.5 mm, 0.6-1 mm. In the example detector of FIG. 8, the diameter is about 0.8 mm.

In certain implementations, the diameter 364 of each of each well 355 can be selected based on the thickness 353 of the dielectric layer 352. In certain embodiments, a ratio between the diameter and thickness can be in a range of about 1/10 to 1/1. In certain embodiments, the ratio can be in a range of about 1/4 to 1/3. In certain embodiments, the ratio can be about 1/3. Thus, in certain embodiments, the diameter can be based on such ranges of ratios based on the foregoing example ranges of dielectric layer thicknesses.

In certain implementations, the pitch 363 or the spacing between the edge of one well to the edge of a neighboring well can be selected based on factors such as a desired density of wells and/or the diameter of each well. In certain embodiments, the pitch 363 can be in a range of about 1-10 mm or about 2-5 mm.

In certain embodiments, a ratio between the pitch 363 and the diameter 364 can be about 1 to 5 or about 1.1 to 3. For example, in one embodiment, the diameter 364 can be about 0.8 mm; thus, the pitch 613 can be about 2 mm.

In certain implementations, a detection array can include from about 50-10,000 wells 355. The number of wells can be greater or lesser than such an example range.

An upper readout electrode strip 360 is provided to each row of wells and held at ground potential. A lower readout electrode strip 361 that extends perpendicular to the upper strip 360 is also provided. The upper and lower readout strips 360, 361 provide a 2-dimensional readout capability for the wells 355.

Figure 9A:
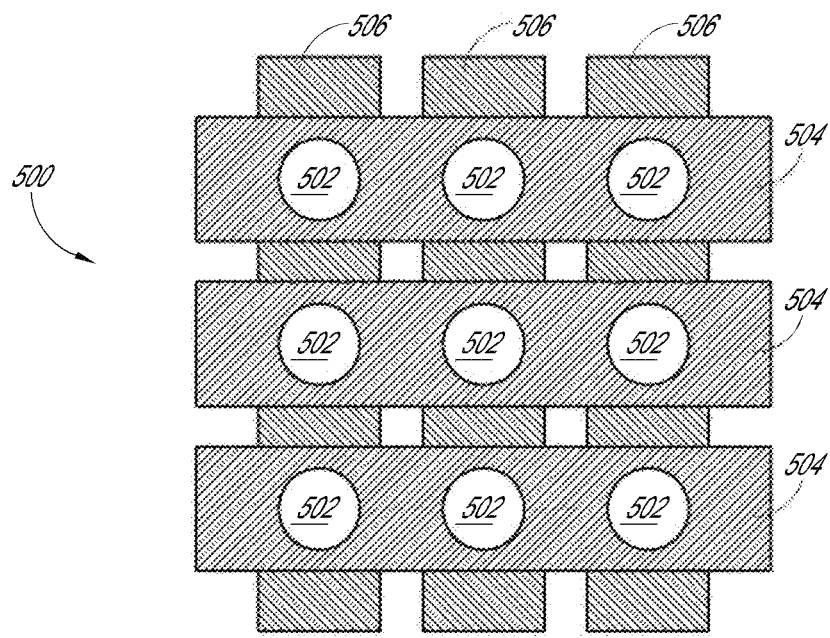
FIGS. 9A and 9B show examples or readout electrode strips that can be implemented in the detector apparatus of FIG. 8.

In certain implementations, readout electrode strips can be configured in a number of ways. FIG. 9A shows an example configuration 500 that can be similar to the configuration associated with FIG. 7, where a first set of readout electrode strips 504 extend in a first direction, and a second set of strips 506 in a second direction (e.g., perpendicular to the first direction). Each of the strips 504, 506 can include a number of apertures for accommodating the openings 502 of the wells.

Figure 9B:
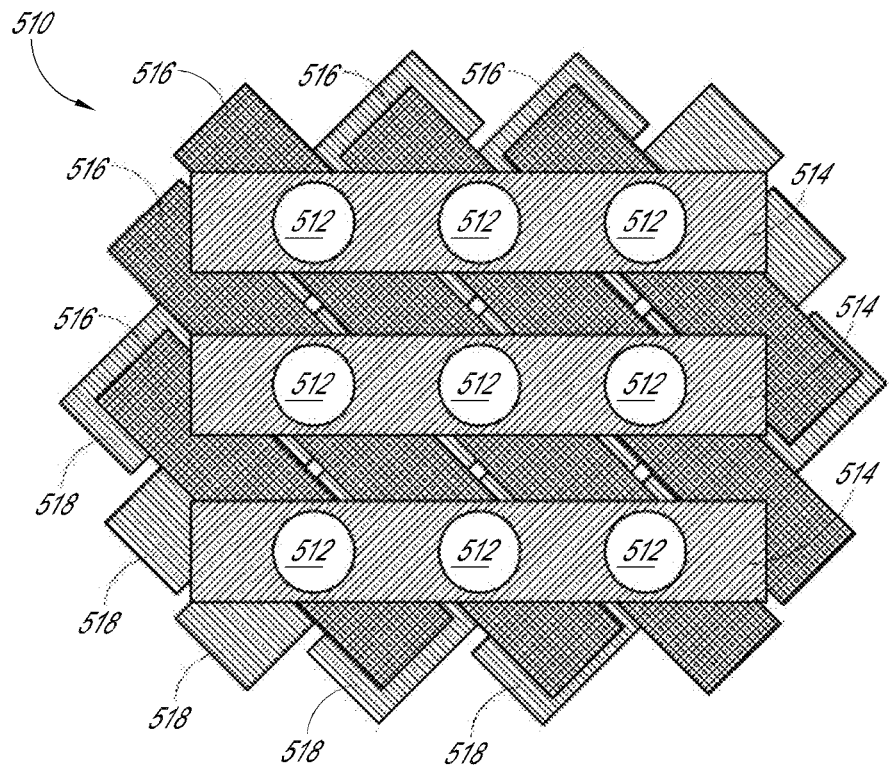

In certain situations, the readout configuration of FIG. 9A can result in ambiguities in hit locations when more than one ion arrives on the array close enough in time (e.g., substantially simultaneously). To address such issues, certain embodiments of a readout configuration 510 (FIG. 9B) can include three or more sets of readout electrode strips. In the example configuration 510, a first set is shown to have strips 514 that extend along a first direction. Second and third sets of strips 516, 518 are depicted as extending along two different directions (e.g, about 135 degrees and 45 degrees relative to the first direction) other than the first direction and a perpendicular of the first direction. Such angled configurations are sometimes referred to as "U" and "V" orientations (in the context of "X" and "Y" orientations of FIG. 9A) can facilitate resolving of the foregoing ambiguities. Such resolving techniques and parameters such as angle selections can be achieved in known manners.

Positive ions, produced in a low pressure (e.g., about 1-10 Torr) working gas above the detector plane, drift to the detector plane under a relatively weak (e.g., about 10-100V/cm) electric field provided by anode (relative to the electrode 354, and not shown) connected to a positive power supply. Focusing of the ions into the detector openings 362, their acceleration and following charge multiplication process in the well gas can be controlled by applying a negative voltage to the lower electrode (cathode 356) which provides a very high reduced-electric field across the well. To prevent damaging discharges and sparks, this electrode can be made of highly resistive material (e.g., glass) and each detector cell can operate under a voltage well below the field emission breakdown threshold.

For the example 3.2 mm-thick dielectric layer 352 shown in FIG. 8, and when the gas used is propane, air or water vapor at about 2 Torr pressure, the voltage applied to the cathode 356 can be in a range of about 650-850V. The resulting reduced-electric field (E/p) in the well is about 2000V/(cm Torr) which is well above charge multiplication thresholds for electrons and ions (about 30 and 70 V/(cm Torr), respectively, in propane).

A restricted avalanche in the well hole can start by positive ion impact ionization and can develop due to ionizing collisions of secondary electrons and positive ions, with the former being responsible for most of the charge multiplication. Ionization cross sections for positive ion impact at low energy (e.g., 10-1000 eV) are scarce; however, available data for light ions (H, He) indicate that ionization cross section for positive ions is about factor 2-10 smaller then for electrons of the same energy. According to an estimate based on observation of ion induced charge multiplication in low pressure gas, a probability for at least one gas ionization on 0.1 mm ion path in 1 Torr propane under an electric field of the order of 1000V/cm is below 10%.

Therefore a micro-pattern detector thickness on the order of about 0.1 mm is likely too thin in some embodiments for high efficiency of single positive ion registration. In certain embodiments, a much thicker (e.g., a few mm) detector structure can provide a high probability of ion impact ionization as an ion passes through the cell.

It is also noted that attempts to increase the ion impact ionization probability by providing higher electric fields can result in field emission breakdowns that can permanently damage detector structures.

After the ion induced ionization occurs, the secondary electron(s) accelerating in the high electric field across the cell can initiate an avalanche propagating to the top of the cell. In such a high electric field, the process, once started, goes on until substantially all of the gas in the cell is ionized. A discharge can develop, unless the electric field is restricted by space charge effects or by an external device or circuit (e.g., a resistor in the HV bias chain). In certain embodiments, the discharge stops when the voltage across the cell drops due to the high volume-resistivity of the cathode 357. This effect is similar to the limited streamer process occurring in, for example, resistive plate chambers (RPC).

The discharge can be restricted not only in time but in space, since it is substantially confined to the cell where it started. Propagation of the discharge due to UV photon feedback can be limited by the cell walls; and the detector's reverse polarity prevents photoelectron emissions from the anode 354.

The avalanche electrons are cramped to the cell because the detector's electric field configuration can change during the discharge development within a hole. It can be a dynamic process that can be characterized on the basis of the electron trajectories described in reference to FIG. 7 before and close to the end of the electron part of discharge. The fired cell field can change (e.g., drop) because the vast majority of secondary electrons produced at the top of the cell (avalanche head) can be promptly collected on the readout strips, and the non-compensated positive charge of the avalanche ions can be screening the negative potential of the cathode at the bottom of the cell. The field of non-fired neighboring cells can expand to the vacant region, trapping remaining electrons within the fired cell, and deflecting any subsequently arriving ion into a nearby vacant cell. The remaining electrons in the fired cell can be collected on the strips in the weak field configuration or recombine with the ions slowly moving down to cathode positive charge cloud.

A recovery time of the fired cell can depend on the charge collection time and recharging time, and is estimated to be in the sub-µs to the µs range. This fired cell recovery time should not affect the ion detection efficiency because ions will likely arrive sufficiently spaced in time, due to their relative low drift velocities (e.g., about 1 mm/microsecond in 2 Torr propane, at 100 V/(cm Torr)). Further, as mentioned above, ions arriving during cell discharge are likely deflected to the neighbor cells.

In certain embodiments, a signal from the readout strip can be determined by the charge accumulated in the cell's capacitor. Such a charge can be estimated as $Q_{cell} = C_{cell} V$, where C is the capacitance and V is the operating voltage. Cell capacitance in the example detector 351 is on the order of a few tens fF (femtofarad). Thus, for V of about 700V, charge ($Q_{cell}$) values in the tens pC range can be expected.

FIG. 8 shows a detector 150 that includes the various features described in reference to FIG. 8. The example detector 150 can be manufactured using multilayer printed circuit board (PCB) technology. The example detector 150 includes an array 152 of holes 154 that form detection cells (355 in FIG. 8). As previously mentioned, the example detector 150 has a thickness of about 3.2 mm. Further, the array 152 has an active detection area of approximately 2 cm×5 cm. There are 576 holes (154) in the array 152.

To verify the signal amplitude representative of the charge (0 cell) output from a cell, the detector 150 of FIG. 8 was used. More particularly, the detector PCB was mounted on a Teflon base with embedded glass cathode, so the HV electrode surface was exposed to working gas only through detector holes. The detector assembly was then installed into a drift chamber enclosure providing controllable gas environment of about 0.1-10 Torr pressure and a drift field of up to 1000V/cm. The chamber was also equipped with a collimated Am-241 alpha source and a Si detector defining alpha particle beam of about 2 mm in diameter and generally parallel to the detector plane and about 5 mm above it. With this set-up (schematically depicted in FIG. 10A), signals from the top electrode were acquired as negative pulses having about 200 ns duration with amplitude of about 10 mV on a 50-Ohm load. Such a signal is representative of electron charge of about 20 pC, which is generally consistent with the tens pC range expected. The observed signal amplitude corresponds to avalanche charge on the order of about $10^8$ electrons, which is well above the Raether limit for breakdown in gases. That is, each cell can operate as an independent Geiger micro counter.

Measuring average ion arrival time at different anode voltages (hence different ion drift field and velocity), it was verified that the registered ions came from the alpha particle track. The ion drift time distributions measured at anode voltages of 100V and 10V are shown in FIG. 10B. Also measured was the total background rate of the detector resulting from sporadic discharges and ions from cosmic and background radiation. For these measurements a working gas volume (about 2.5×5×5 $cm^3$ filled with propane at 2 Torr) was used. The background rate did not exceed 1 Hz for all of the 576 cells. These results show that the 2-dimensional detector of FIG. 8 can be utilized as a planar ion detector in an ion time projection chamber (TPC).

Figure 11A:
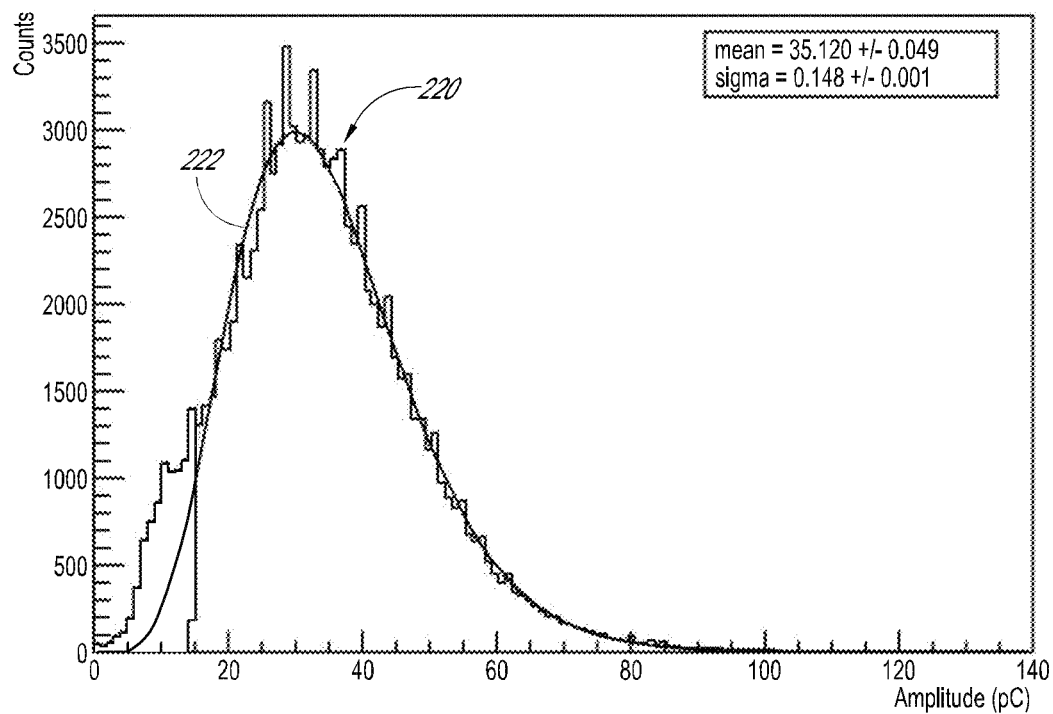
FIG. 11A shows an example distribution of charge resulting from the detector of FIG. 8 operating at approximately 800 V in propane at approximately 3 Torr pressure.
Figure 11B:
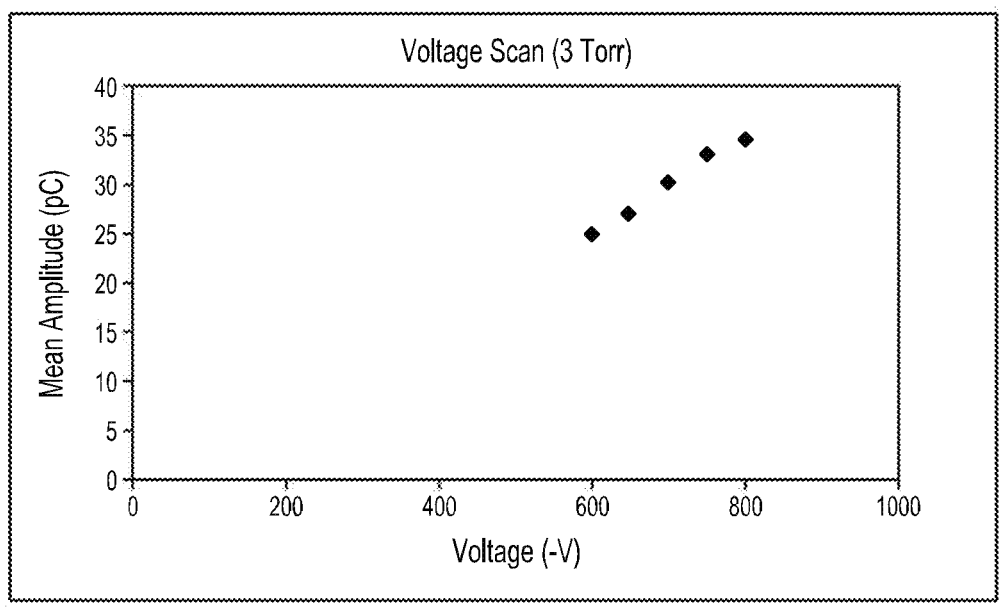
FIG. 11B shows that in certain implementations, the mean signal amplitude corresponding to the charge output of FIG. 11A can depend on the operating voltage.

FIGS. 11A and 11B show other examples of characterizing signal amplitudes representative of the charge ($Q_{cell}$) output from a cell of the detector 150 (FIG. 8). The data 220 shown in FIG. 11A were obtained with the detector operating at about 800V and in propane held at about 3 Torr. The data 220 is fitted with a Polya distribution 222 that is commonly used to characterize single-charge initiated avalanche processes.

As shown in FIG. 11A, the fit distribution 222 yields a mean charge amplitude of about 35 pC, which is also generally consistent with the tens pC range expected. Such a consistency between the estimated range (tens pC) and data continues at other operating voltages as shown in FIG. 11B. A number of mean charge amplitude values are plotted as against operating voltages. As shown, the measured charge amplitudes are in a range of about 25 pC to 35 pC for voltages in a range of about 600V to 800V. Further, the output charge amplitude increases linearly as a function of voltage, also as expected.

In certain implementations of the present disclosure, radiation-induced ionization patterns in condensed matter and in equivalent gas models and of transport and multiplication processes within the different detectors can be simulated. Monte Carlo radiation-transport codes can be applied for improving or optimizing the detector design and for evaluating its performance. Monte Carlo track structure codes can be improved to simulate the transport of ions and secondary electrons in gaseous and condensed media. The validity of interaction cross sections that are used in Monte Carlo codes can be tested using data from the detectors.

In certain implementations, the example ion induced impact ionization detector described in reference to FIGS. 7 and 8 or a similar detector device can be utilized to obtain experimental track-structure data associated with different radiation fields. Such experimental data can be obtained at a number of facilities, including but not limited to, Loma Linda University's proton synchrotron (where protons up to 250 MeV can be provided), Crocker Nuclear Laboratory at UC Davis (where protons and light ions of low and intermediate energies can be provided from its 76 inch isosynchronous cyclotron), and Brookhaven National Laboratory—NASA Space Radiation Laboratory (where protons and heavy ions up to several GeV can be provided from the AGS Booster).

In addition to the foregoing examples of charged particle beams, data can be obtained with radioactive sources including alpha, beta (electron) and gamma sources, representing a wide range of linear energy transfer (LET) values. Nanodosimetry data from a low-intensity radioactive neutron sources can also measured. Thus, a nanodosimetric track-structure database for validations and practical applications can be developed and/or maintained.

Track-structure data measured with the example ion induced impact ionization detector described in reference to FIGS. 7 and 8 has been shown to be useful for estimating radiation effects observed in DNA and producing meaningful quality factors for radiation protection. Measurements were made for frequency distributions of ionization event sizes within a nanometric sensitive volume with rough dimensions of a DNA segment (about 4 nm diameter, FWHM and about 20 or 47 base pairs long) under various geometrical beam conditions. As described herein, FIGS. 2A and 2B show examples of nanodosimetric event size distributions measured for various primary ions and energies, and a comparison of experimental and Monte-Carlo simulated distributions for protons. There is a good agreement between the measurements and simulations, down to frequencies of about $2 \times 10^{-3}$ (which corresponds to about 6 ions per cluster). For larger clusters, there appears to be an excess of measured ions with respect to the simulation results.

While it is not desired or intended to be bound by any particular theory, some experimental results suggest that these additional ions seen in the foregoing experimental distribution may be caused by a rare gas multiplication process which takes place in the intermediate vacuum of the ion acceleration channel below the detection cell aperture.

Additional studies correlating nanodosimetric data of various radiation fields with radiochemical and radiobiological data can validate various methodologies and translate such validated methodologies into practical applications. Utilizing one or more of the foregoing radiation fields, data for a number of more specific applications can be obtained; and such applications can include radiochemical yields of clusters of hydrogen peroxide or other stable radiolysis products in nanoparticles; DNA double strand break and other complex damage yields in DNA model systems; DNA double strand break and other complex damage yields in cells; CNS effects in suitable animal models; Cancer induction in suitable animal models. Additionally, existing in vitro and in vivo data can be used to test nanodosimetric prediction models.

In certain implementations, one or more of the features described herein allows imaging of a track passing through a volume of gas, which in turn can be scaled into tissue-equivalent (TE) scales and units. For such systems, resolution of positive ion imaging can be estimated.

Constraints imposed by ion diffusion on a track imaging detector can be represented in tissue-equivalent (TE) units defined by the scaling factor kp, where p is the pressure and k is a gas-dependent "dE/dx" scaling factor of an order of about $10^{-6}$-$10^{-7}$. On the TE scale, the rms broadening due to a drift distance $l_{TE}$ can be represented as:

$$\Delta x_{TE} = \sqrt{k}\,\sqrt{2l_{TE}}\,\sqrt{\frac{D/K}{E/p}}$$

where D, K, and E represent the ion diffusion, ion mobility and electric field, respectively.

Figure 12:
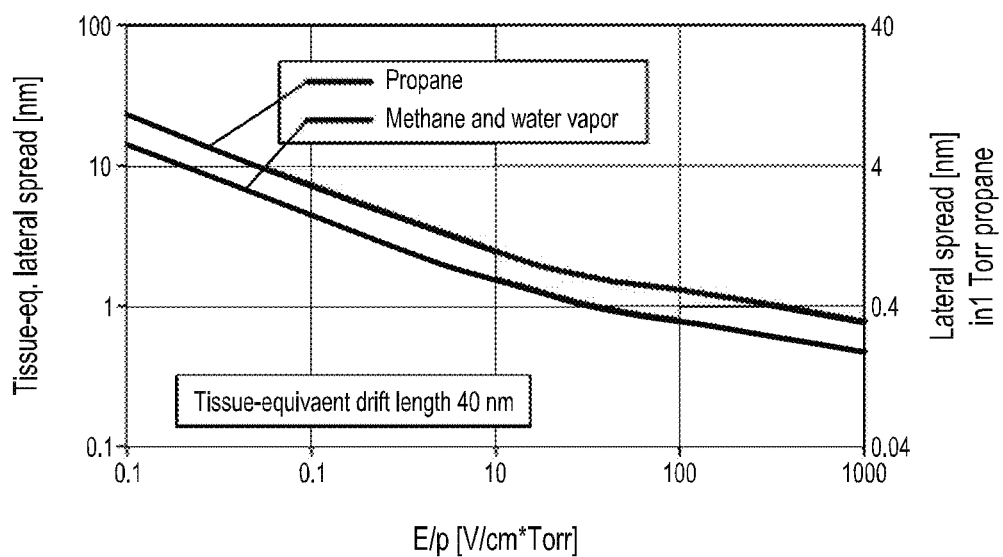
FIG. 12 shows example plots of lateral resolution (rms) in tissue-equivalent (TE) units for ions following a drift path of approximately 40 nm in approximately 1 Torr propane.

Based on average D/K values, the rms TE resolution, $\Delta x_{TE}$, can be estimated as a function of E/p. Such an estimate is depicted in FIG. 12 for different gases. For a reasonable E/p value (e.g., approximately 100 V/(cm Torr) used in at least some of the configurations described herein), one can expect a typical TE resolution of ≤1.4 nm (rms) when an upper limit of TE drift distance is about 40 nm. Methane or water vapor can yield even a better resolution, provided that a sufficiently high reduced-field can be maintained in these gases.

In a laboratory frame, gas pressure can define or influence actual dimensions and resolution of a detector, including the upper limit of drift length, $l_{LAB}$, and the resolution $\Delta x_{LAB}$, which in turn can provide design parameters (e.g., pitch and/or cell size) related to pixelization of a detector's array of cells.

For example, at a pressure of about 1 Torr propane, the resolution limit due to ion diffusion is estimated to be about 0.5 mm (rms) for a drift of about 15 mm, thus a cell size of about 0.2 mm² can be adequate. In some situations, increasing the pressure will not improve the resolution on the TE scale, but will reduce it in the laboratory frame if the pixel size remains unchanged. Consequently, a detector with smaller pixelization will be needed in such a case to provide the same TE resolution. Also, in some situations, the dimensions of the detector and the drift length can scale with pressure, affecting the overall detector design.

In certain implementations, the gas choice and the reduced-electric field can define the ion diffusion and the resolution $\Delta x_{TE}$, on the TE scale for a given upper limit of TE drift length $l_{TE}$, which in turn can be defined by the type of radiation to be imaged (e.g., $l_{TE}$ of about 16 and 40 nm for 1 and 100 MeV protons, respectively). A typical value of the rms TE resolution for ions drifting over the upper limit of TE drift length of about 40 nm in propane can be about 1.4 nm or better.

In certain implementations, the present disclosure relates to systems and methods for characterizing radiation in a manner that approximates interactions between radiation and nano-scale condensed matter. A DNA molecule is an example of such a nano-scale condensed matter. There are a number of other materials and situations where one or more techniques of the present disclosure can be applied.

Figure 13:
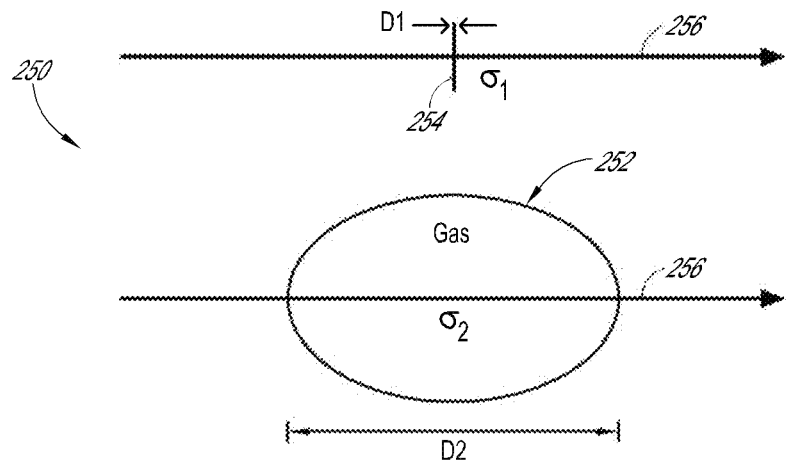
FIG. 13 schematically depicts an example application where interactions of radiation in a volume of low pressure gas can provide an estimate of an equivalent dose of the radiation delivered to a nano-scale condensed matter.

FIG. 13 schematically depicts a radiation measurement configuration 250 where ionizing radiation (arrow 256) passes through a gaseous interaction region 252. For the purpose of description, the interaction region 252 can include one or more types of gases generally maintained at a selected pressure or within a range of pressure so as to provide an interaction cross-section $\sigma_2$ representative of a probability of ionizing interaction between the ionizing radiation 256 and the gas molecules or particles. Also, the interaction region 252 is depicted as having a dimension of D2 generally along the direction of the ionizing radiation 256.

In certain embodiments, and as described herein by way of examples, configuration of the gas and the interaction region dimension D2 can be selected so as to approximate interaction of the ionizing radiation 256 with a much smaller and denser material such as a nano-scale condensed matter 254 (depicted as having an interaction dimension of D1). In certain embodiments, dimension and/or density scaling between the nano-scale interaction and the measured interaction can be achieved by making equivalent the interaction probabilities during passages through the nano-scale condensed matter 254 (dependent on cross-section $\sigma_1$) and the gaseous region 252.

As described herein, such scaling can allow representative measurements and characterization of nano-scale materials in more manageable and/or convenient detection formats. For example, in situations where detector elements having millimeter range dimensions are utilized to approximate and characterize interactions in nano-meter range dimensions, there can be an effective detection volume scaling expansion by a factor of about 1 million.

Figure 14:
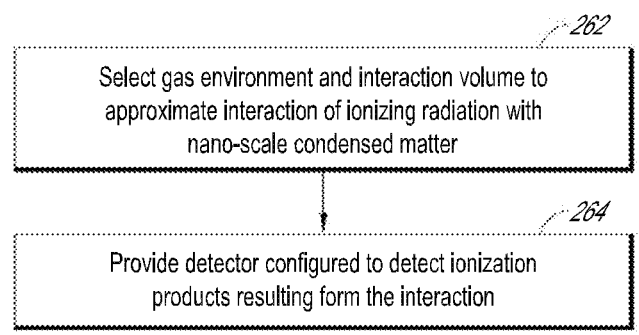
FIG. 14 shows an example process that can be implemented to facilitate the dosimetry system of FIG. 13.

FIG. 14 shows that in certain implementations, a process 260 can be implemented to achieve such a scaled expansion of detection volume. In a process block 262, gas environment and interaction volume can be selected to approximate interaction of ionizing radiation with a nano-scale condensed matter. In a process block 264, a detector can be provided and configured to detect ionization products (e.g., positive ions) resulting from the interaction.

Figure 15:
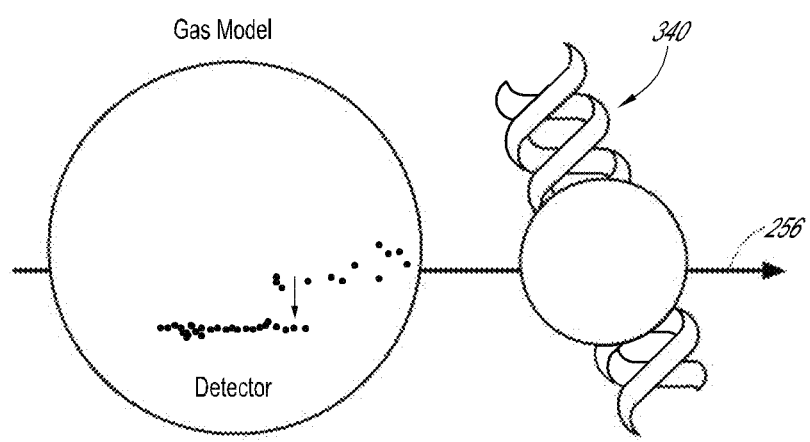
FIG. 15 shows that in certain implementations a gas model can simulate a condensed matter such as a DNA molecule, thereby allowing characterization of its interaction with radiation at a large expanded scale.

FIG. 15 schematically depicts an example of characterization of a smaller-scale matter (e.g., a nano-scale condensed matter) to a larger-scale detection volume. As shown, the example nano-scale condensed matter can be a DNA strand 340, through which radiation 256 passes. Such an interaction of radiation 256 with the DNA strand 340 is shown to be characterized by characterizing the interaction of the same or similar radiation with a gas detector volume. Detection of ionization products such as positive ions and characterization of the radiation track through the gas detector volume can provide a gas model representation of how radiation 256 interacts with the DNA molecule. Because the gas model can be based on more practical detection parameters (e.g., mm range dimensions, gas choice, gas pressure, modes of detecting ionization products, etc.), modeling and characterization of radiation's interaction with a nano-scale sized object such as a DNA strand can be achieved in a more controlled and practical manner.

Figure 16:
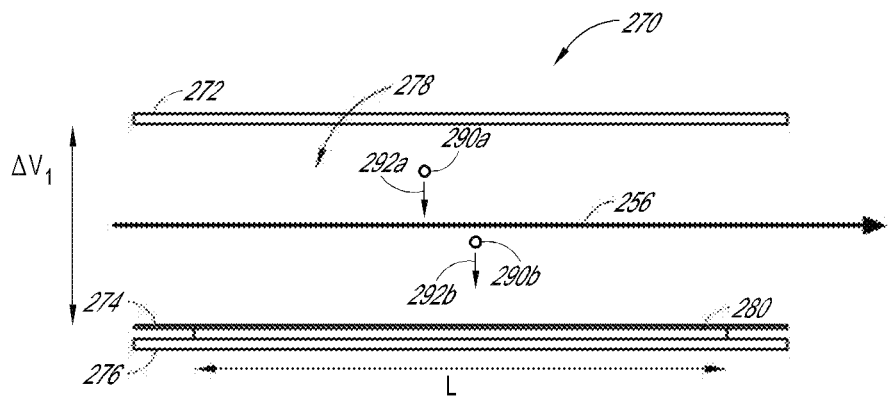
FIG. 16 shows an example configuration of an interaction volume of gas where ionization products can be generated, collected and detected.

In certain embodiments, one or more features described herein can be implemented in a detector capable of detecting spatial information for incident radiation (e.g., charged particles). FIG. 16 schematically depicts how a gaseous interaction volume 278, representative of the volume 252 in FIG. 13, can be configured so as to allow detection of ionization products (e.g., positive ions 290). In certain embodiments, an interaction apparatus 270 can include first and second electrodes 272 and 274 arranged to allow passage of ionizing radiation 256 through the gaseous volume 278 defined between the electrodes 272 and 274. The electrodes 272 and 274 are shown to be held at a potential difference of $\Delta V_1$.

The interaction apparatus 270 is further shown to include a detector layer 280 disposed between the second electrode 274 and a third electrode 276. The detector layer 280 and the associated electrodes 274, 276 can be configured in manners similar to those described herein (e.g., FIGS. 7 and 8).

The second electrode 274 can act as a ground, and the first electrode 272 can be held at a selected positive voltage $+\Delta V_1$ relative to the ground. Thus, for the gaseous volume 278, the first electrode 272 can act as an anode, and the second electrode 274 as a cathode.

The third electrode 276 can be held a selected negative voltage $(-\Delta V_2)$ relative to the ground. Thus, for the detector layer 280, the second electrode 274 can act as an anode, and the third electrode 276 as a cathode.

The potential difference $\Delta V_1$ for the gaseous volume 278 can be selected so as to provide a relatively weak electric field (e.g., about 10 to 100 V/cm) for a given gas type and pressure. Such a relatively weak electric field can facilitate drifting (depicted as arrows 292) of positive ions 290 generated from ionizing interactions and/or secondary interactions, without promoting charge multiplication processes within the volume 278.

The potential difference $\Delta V_2$ for the detector layer 280 can be selected to promote such charge multiplication processes. Various design considerations associated with such potential difference (such as gas type, gas pressure, spacing between electrodes) are described herein in greater detail.

In certain situations, it may be desirable to be able to detect single ionization events. In each of such events, a positive ion and an electron are generated from ionization. As described herein, such positive ions from ionized gas molecules can be detected with single-ion resolution, so as to allow characterization of radiation interaction effects such as formation of large ionization clusters that contribute to damages to materials such as DNA strands.

Figure 17:
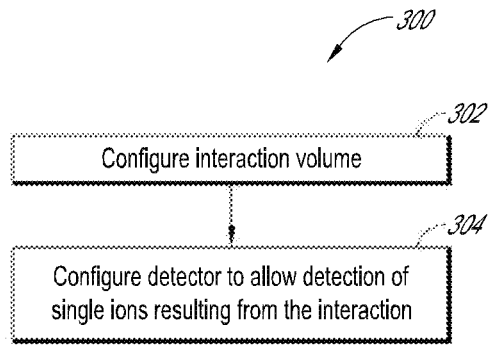
FIG. 17 shows an example process that can be implemented to facilitate detection of single ions resulting from events such as the ionization occurring in the gas interaction volume of FIG. 17.

FIG. 17 shows a process 300 that can be implemented to facilitate such single ionization event characterization. In block 302, an interaction volume can be configured as described herein. In block 304, a detector (e.g., detector layer 280 and associated electrodes in FIG. 16) as described herein can be configured to allow detection of single ions generated in the interaction volume.

Figure 18:
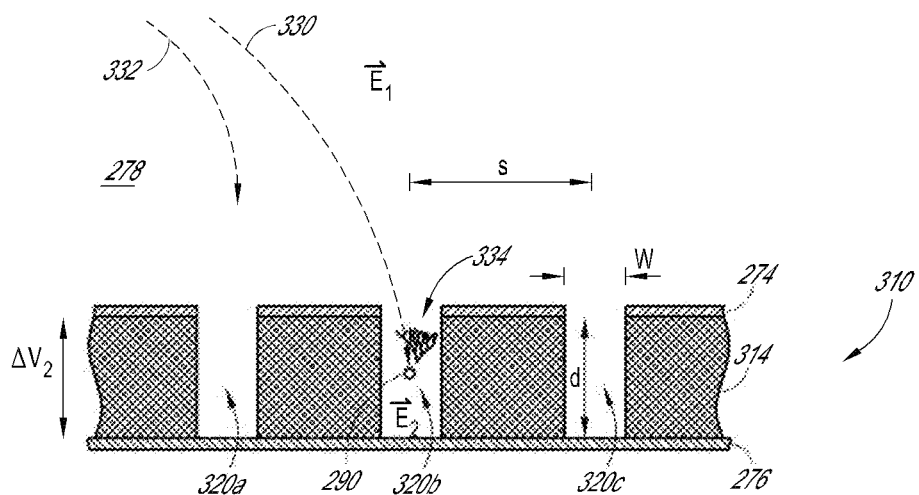
FIG. 18 shows an example configuration of a well based detector that can achieve detection of single ions.

FIG. 18 schematically depicts a portion of a detector 310 that can be configured to provide such a single-ion detection capability. Further, the detector 310 can have an array of detection elements to allow spatial characterization of the ionizing interactions occurring in the interaction volume.

As shown, the detector 310 can include a plurality of wells 320 defined between two electrodes 274 and 276. In certain embodiments, the electrodes 274 and 276 can be the second and third electrodes, respectively, described herein in reference to FIG. 16. Additional details about the electrodes 274 and 276 (including an example of array readout scheme via the ground electrode 274) and electric fields generated by the electrodes are described herein in greater detail.

In certain embodiments, the wells 320 can be formed on an insulating layer 314 such as a dielectric layer. The example wells 320 in FIG. 18 are depicted as having a depth "d," a width "w," and an inter-well spacing "s." Selections of such dimensions are described herein in greater detail. In certain embodiments, the wells 320 can be open on the side facing the interaction volume 278 such that gas pressure in the wells 320 can be generally same as that of the interaction volume 278. Such a feature can simplify the design and operation of the detector 280.

In the example configuration shown in FIG. 18, a single ion 290 from an interaction (not shown) in the volume 278 is depicted as drifting (dotted line 330) into the well 320b. Due to the electric field $E_2$ provided by the electrodes 274 and 276, and/or the gas configuration, the entering ion 290 can accelerate towards the cathode 276 and result in multiplication of charges (e.g., avalanche 334) substantially in the well 320b. Details about such electric field and gas configurations, as well as charge multiplication processes and detection thereof, are described herein in greater detail.

As also described herein in greater detail (e.g., in reference to FIGS. 6A and 6B), electric field formed at or about a given well opening can change dynamically as ion-induced charge multiplication occurs in the well (e.g., in 320b). Such a dynamic nature of the electric field can promote substantial containment of generated charges in the well, and also promote deflection of additional incident ion(s) to other unoccupied well(s). For example, the charge multiplication process in well 170b can result in an electric field change that promotes deflection of another incident ion (depicted as dashed line 332) into another unoccupied well (e.g., a nearby well 320a).

In certain implementations, an ion detector such as the example detector 310 of FIG. 18 can be configured to be a part of system. Such a system can be configured to detect ions (primary and/or secondary) so as to allow characterization of interactions and/or processes that generate such ions. By way of an example, FIG. 19 shows a process 370 that can be configured to characterize interactions of ionizing radiation with a volume of low pressure gas by detecting ion products.

As described herein, such characterization of the interactions in low pressure gas can be utilized for track-structure study of a number of radiation-matter interaction settings. Such a study is sometimes referred to as ionization pattern imaging, and can be applied to characterization of ionizing radiation with nano-scale condensed matter objects such as DNA strands.

Figures 19, 20:
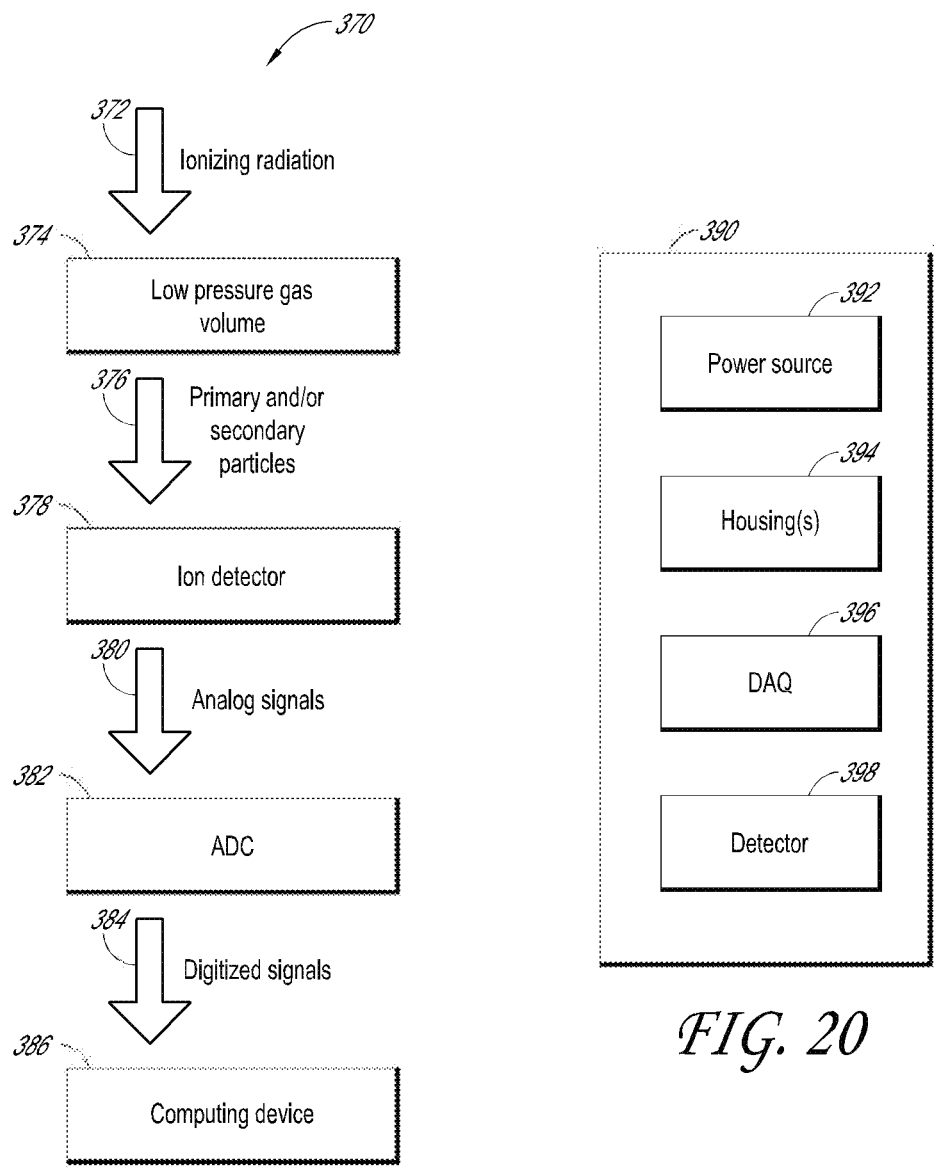
FIG. 19 schematically depicts an example of how data can be acquired from detection of ions in an analytic system.
FIG. 20 schematically depicts various components that can be provided to a system capable of facilitating the process of FIG. 19.

Referring to FIG. 19, the process 370 shows ionizing radiation (arrow 372) entering a low pressure gas volume 374 and interacting with the gas therein. Interaction products such as primary and/or secondary ions (arrow 376) can be detected by an ion detector 378. In certain embodiments, such interaction products can be subjected to electrical and/or magnetic field to move (e.g., drift or accelerate) the ions to the detector. The detection of the ions can yield analog signals (arrow 380) from the detector 378, and such signals can be converted to digital signals 384 by an analog-to-digital converter (ADC) 382. Such digitized signals can be provided to a computing device 386 for further processing and/or analysis.

In certain embodiments, a system 390 having a number of components can be configured to facilitate the example process 370 of FIG. 19. The system 390 can include a power source 392 for providing power to, for example, electrodes that define drift electric field in the interaction gas volume and ion detecting electric field in each of a number of detection cells. The system 390 can further include one or more housing components 394, including, for example, a housing configured to provide the interaction gas volume. The system 390 can further include a data acquisition (DAQ) component 396 configured to provide, for example, readout of signals from an array of detection cells and conversion of such signals into representative digital signals for further processing by a computing device. The system 390 can have a detector component 398 configured to provide one or more detector features and/or capabilities as described herein.

In certain implementations, the foregoing detector component 398 can be based on one or more ion detector elements that are configured to allow efficient detection of single ions. FIG. 21 schematically depicts such a detector element 400.

In certain embodiments, a number of such detector elements 400 can be arranged in an array to allow spatial determination of ions' incidence locations on the array. FIG. 22 schematically depicts such an array 410 of detector elements 400.

In certain embodiments, such an array of ion detector elements can be used in an analytic system having an ion detection component. FIG. 23 schematically depicts such a system 420 having an ion detector array 410.

There are a number of analytic systems where the ion detector array 410 can be implemented. FIGS. 24A-24C show some non-limiting examples of the analytic system of FIG. 23. For example, FIG. 24A shows a dosimeter system 430 having the ion detector array 410. Various configurations and operating parameters are described herein in the context of such a dosimeter system. However, similar detector elements and arrays thereof can also be implemented in other analytic systems.

In certain embodiments, FIG. 24B shows that a mass spectrometer 440 or a similar system can include the ion detector array 410 for detecting ions. For example, ions that undergo mass separation due to electric and/or magnetic field(s) can be detected by the detector array 410 and spatial separation of the detected ions can be analyzed for mass identification.

In certain embodiments, FIG. 24C shows that a gas chromatograph 450 or a similar system can include the ion detector array 410 for detecting ions. For example, ions that emerge from a column exit can be detected by the detector array 410 for analysis.

As used herein, mass spectrometry can include an analytical technique for determining the elemental composition or structure of a sample or molecule. Mass spectrometers can include an instrument used to implement analytical techniques of mass spectrometry. As used herein, gas chromatography can include an analytical technique for separating compounds in a mixture, wherein the mixture is vaporized but not decomposed. A gas chromatograph can include an instrument used to implement analytical techniques of gas chromatography.

The ion detector element and/or an array formed by such elements can be utilized in other systems. For example, ion detection configurations as described herein can be implemented in systems for detecting very low concentrations of chemicals. An ion mobility spectrometer is an example where trace concentrations of chemicals such as explosives, drugs, and chemical weapons can be detected. Such spectrometers can include one or more features of the ion detectors as described herein to allow efficient and accurate characterization of ions.

In some embodiments, the ion induced impact ionization detector can be capable of providing new valuable data in the field of detector physics, related to ion interactions with gases and solids, light emission, multiplication processes in gas and advanced radiological imaging techniques.

Some embodiments as described herein can be directed to a high-resolution, high-sensitivity 3D imaging track structure imaging devices operating with low-density gases. The ion induced impact ionization detectors as described herein can facilitate characterization of the interaction of ionizing radiation with matter in the condensed phase. In one aspect, an approach to such a characterization can be based on experimental techniques, such as nanodosimetry, and Monte Carlo (MC) track structure simulations. One can then, for example, relate the gas phase track structure and condensed phase track structure. Such an approach can facilitate finding of track structure characteristics on the micro- and nanometer-scale that are common to both phases and are relevant for the effects of ionizing radiation on living cells and DNA nanostructures. In some implementations, experimental track structure data may be used to benchmark MC codes.

As used herein, condensed matter can include cells, tissues, polymers, nanoelectronics and nucleic acid molecules such as DNA, in which an aberration may be induced. As used herein, aberration can include local damage to condensed matter associated with ionization clusters that have been identified. As used herein, ionization clusters can include a plurality of ionization products, such as about 2-20 ions per cluster. In some cases ionization clusters can have about 6 ions per cluster.

An example application for radiation medicine and protection can relate to performing high-resolution track-structure studies to obtain an improved mechanistic understanding of radiation damage to DNA and chromosomes. For this, ionization tracks can be recorded in dilute gas with a precision of about one tissue equivalent nm to study clustering of ionizations on the DNA scale and over a track segment length of one tissue-equivalent $\mu$m. Study of these clustering effects for different types of radiation used in radiotherapy (high energy electrons, photons, and light ions) and their comparison with the prediction of Monte Carlo simulations can be used to develop sophisticated mechanistic models of radiation effect on DNA and other important biomolecules.

In some embodiments, a track structure-imaging system can be configured to be capable of highly efficient and precise localization of ionization patterns on these scales. In some embodiments, ionization-induced positive ions can be recorded and deposited in low-pressure gas.

In certain implementations, modeling tissue with a low-pressure gas target can allow expanding tissue scales, according to the "dE/dx ratio" scaling factor up to, for example, about $10^6$ for 1 Torr. Such a scaling factor can be chosen according to the dimensions accessible by available gaseous detectors, and/or the scale of the condensed matter being studied. In some embodiments, a ion induced impact ionization detector configured to provide substantially full track structure and single charge sensitivity can provide a resolution of sub-nm tissue-equivalent precision over a micrometer tissue-equivalent range. The same dimensions can also be relevant to non-biological applications such as those relating to nanoelectronics devices.

As used herein, "nanometer equivalent resolution" can include resolution of sub-nm tissue-equivalent precision over a micrometer tissue-equivalent range and similar dimensions in nanoelectronics devices. Nanometer equivalent resolution may relate to a spatial separation of individual energy-deposition events (e.g., electron-ion, electron-hole pairs) in condensed matter. In some embodiments, the spatial separation can be of the same order of magnitude as the lateral dimensions of a DNA molecule or strand and of some elements in nanoelectronics, i.e., in the nanometer domain. For example, nanometer equivalent resolution includes a precision of about one tissue equivalent nm, where such precision can be useful for study of clustering of ionizations on the DNA scale and over a track segment length of one tissue-equivalent $\mu$m.

In certain implementations, the ion detector element 400 of FIG. 21 can be configured to include one or more of the features described herein. In certain embodiments, such features can include those described in reference to FIGS. 7-9.

In certain implementations, such an ion detector element 400 can be operated in a limited Geiger mode (e.g., fired/not fired). In certain implementations of such an operating mode, one or more features associated with the ion detector element 400 can be configured to provide a gas environment that under super-stress by the electric field applied to the well of the detector element 400. Such a state can be analogous to a super-cooled or super-heated state of liquid, where the phase transition (freezing or boiling) has not occurred even after the temperature has gone below the freezing temperature or above the boiling temperature. In such a state, a slight disturbance and/or a seed condition can trigger a rapid phase transition.

In certain implementations, the super-stressed gas environment of the ion detector element 400 can be achieved by providing an electric field to the well so that the electric field strength is higher than a threshold value or range of values associated with breakdown of gas. Such a threshold value or range can depend on factors such as type of gas, pressure and/or temperature. In certain implementations, the electric field strength can be selected to be also higher than a threshold value or range of values associated with ion multiplication. Such a threshold value or range is typically higher than the corresponding gas breakdown threshold value or range.

In certain implementations, the electric field strength can be selected based on one or more of the foregoing threshold values, and to be lower than a threshold value or range of values associated with field emission breakdown at a surface of the well. Such a value or range can depend on the material associated with the well surface.

Voltages associated with the foregoing electric field strengths can depend on factors such as separation distance of the electrodes and electrode geometries. Thus, an applied voltage can be selected for a given well size (e.g., depth), gas type, gas pressure and/or gas temperature so as to yield a desired electric field strength having one or more of the foregoing properties.

For example, the example detector configuration of FIG. 8 can be supplied with a voltage of about 600 to 900 V between the electrodes to yield a desired gas condition when the detection configuration includes propane, air or water vapor at about 2 Torr in a well having a depth of about 3.2 mm.

In certain detection situations, sensitivity of a detector and its stability can be balanced. For example, a detector configured to be highly sensitive can be triggered easily by a particle (e.g., an electron) other than a desired particle (e.g., an ion). In the context of the super-tensioned gas environment, an electron can easily trigger the limited Geiger process. In certain implementations of the present disclosure, however, likelihood of such electrons entering the well of an ion detector element (e.g., 400 in FIG. 21) can be reduced by a reversed polarity of the voltage biasing configuration.

Figure 10A:
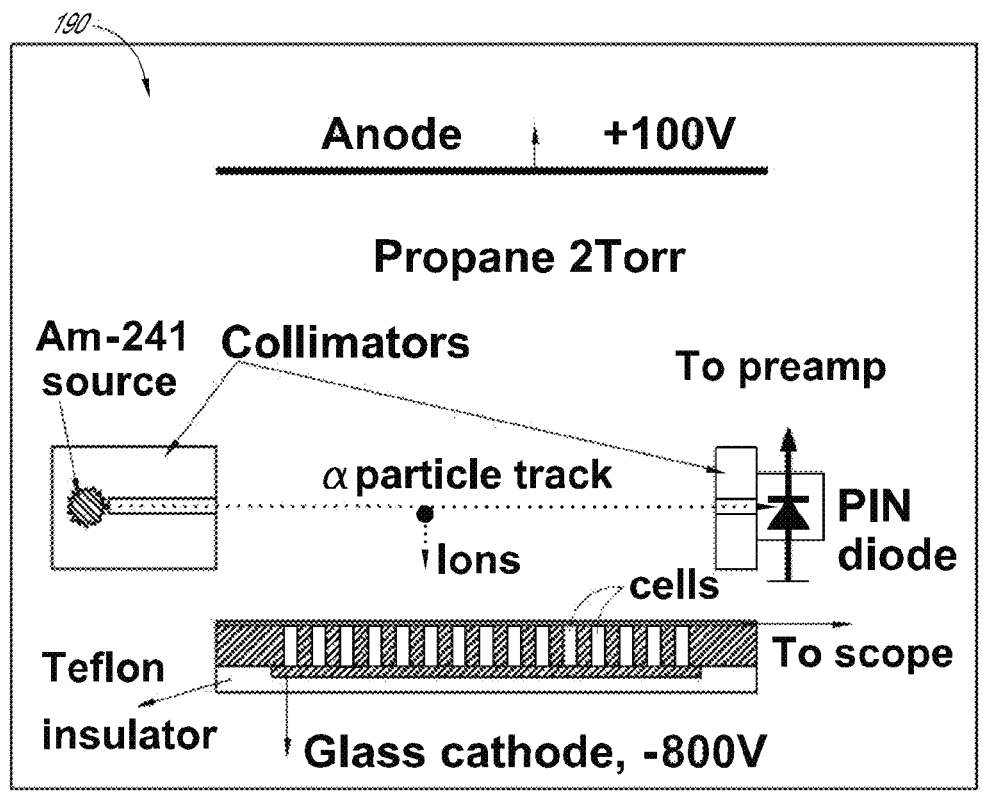
FIG. 10A shows an experimental setup using alpha-particles for testing the detector of FIG. 8.
Figure 10B:
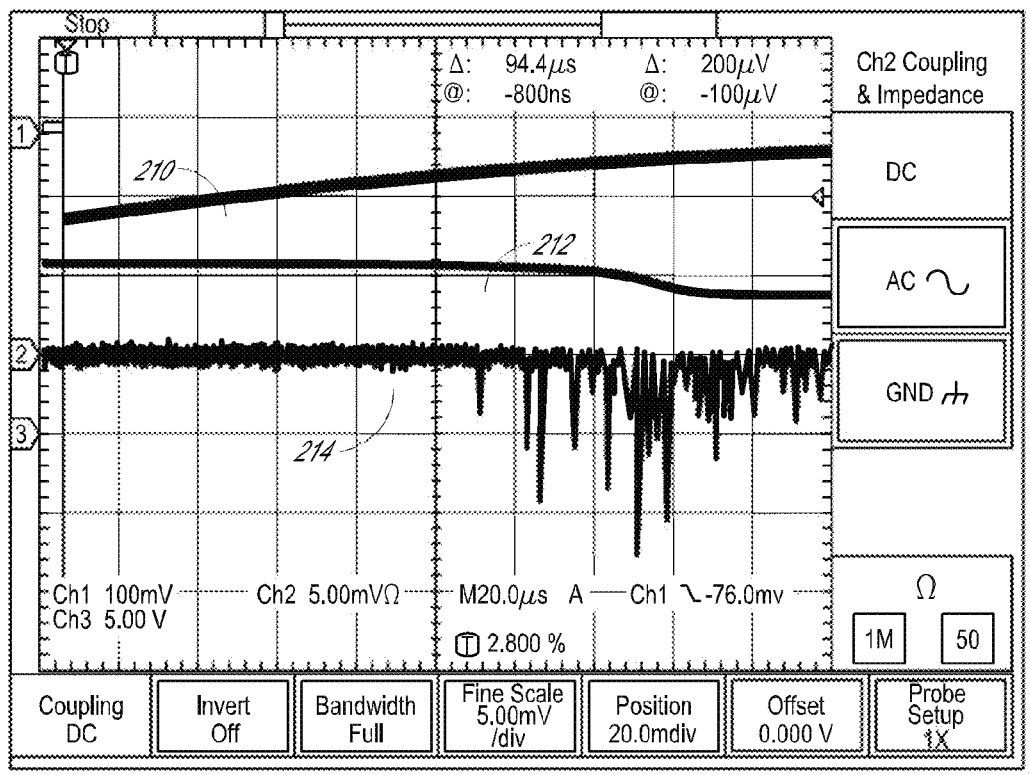
FIG. 10B shows examples of signals that can be extracted from the example setup of FIG. 10A.

For example, and referring to FIGS. 10A, 16 and 18, certain embodiments of the present disclosure can be configured so that the deep end of a well can be held at a negative potential relative the well's opening. Further, an anode that facilitates drifting of positive ions towards the detector can be held at a positive potential relative to the well's opening. Accordingly, electrons in the vicinity of the well will be subjected to a force that directs electrons away from the well (towards the anode).

In certain embodiments, an ion detection cell having one or more of the features described herein can operate with a relatively large dead time typically associated with the Geiger operation mode. Despite such a property, a high detection efficiency for single ions can be provided by use of a large number of such cells distributed and configured to reduce the likelihood of two or more ions entering a single detection cell.

Further, due to the diffusion of ions generated in a low-pressure gas volume, even ions originating from the same deposition point are likely to be registered in different cells. Hence, the effective efficiency can be relatively high.

As used herein, a gas can include multi-atomic gases and gas mixtures to simulate biological and semiconductor media. For example, a gas can include one or more of the following gasses: propane, ambient air, and water vapor. In certain implementations, the gas can be ionized by initiating an avalanche breakdown of gas in a well, whereby the ionizing induces charges that are multiplied thereby forming a detectable signal.

As used herein, low pressure or low pressure gas can include a gas at a pressure that is less than about 100 Torr. In certain implementations, low pressure can include a pressure in a range of about 1 to 10 Torr.

As used herein, a breakdown potential can include a point at which non-conducting gas becomes conductive as governed by the pd product (p=pressure, d=inter-electrode gap distance) and the Townsend mechanism. In some embodiments, the breakdown potential can occur when an electric field exceeds a particular value, wherein an electron avalanche starts, for example, due to multiplication of some primary electrons in cascade ionization. In some embodiments, the breakdown potential can be about 0.1-1.5 cm Torr at an operating pressure of about 1-10 Torr, and an inter-electrode gap distance of between 2-5 mm. In some embodiments, the breakdown potential can be at a pd value of about 0.6 cm Torr (about 2 Torr and about 3.2 mm gap), for example for propane, air and water vapor, can be about 400-600V assuming a substantially uniform electric field. In some embodiments, the field emission breakdown potential can be above about 5 kV for a detector, wherein no breakdown was observed at pd<0.00003 cm Torr (better than 0.0001 Torr vacuum and 5 kV over 3.2 mm gap).

As used herein, E/p value (electric field strength divided by pressure) as used herein is sometimes referred to as "reduced-electric field." Thus, for example ranges of E and p of about 10-100 V/cm and about 1-10 Torr, respectively, the corresponding reduced-electric field (E/p) can have a value in a range of about 1-100 V/(cm Torr).

The terms "approximately," "about," and "substantially" as used herein represent an amount close to the stated amount that still performs the desired function or achieves the desired result. For example, the terms "approximately", "about", and "substantially" may refer to an amount that is within less than 10% of, within less than 5% of, within less than 1% of, within less than 0.1% of, and within less than 0.01% of the stated amount. The term "at least a portion of" as used herein represents an amount of a whole that comprises an amount of the whole that may include the whole. For example, the term "a portion of" may refer to an amount that is greater than 0.01% of, greater than 0.1% of, greater than 1% of, greater than 10% of, greater than 20% of, greater than 30% of, greater than 40% of, greater than 50% of, greater than 60%, greater than 70% of, greater than 80% of, greater than 90% of, greater than 95% of, greater than 99% of, and 100% of the whole.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times.

The teachings of the invention provided herein can be applied to other systems, not necessarily the system described above. The elements and acts of the various embodiments described above can be combined to provide further embodiments.

While certain embodiments of the inventions have been described, these embodiments have been presented by way of example only, and are not intended to limit the scope of the disclosure. Indeed, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A method for modeling a sample of condensed matter, the method comprising:
    directing ionizing radiation into a volume comprising a low-pressure gas;
    detecting with an ion detector ions resulting from interactions between the ionizing radiation and the low-pressure gas, the ion detector configured to detect events with one or more ions, the ion detector comprising:
        a first electrode;
        a second electrode;
        a dielectric layer positioned between the first electrode and the second electrode, the dielectric layer having a thickness of at least 2 mm; and
        a plurality of wells extending through the dielectric layer;
    identifying a number of ions formed in the volume;
    determining a time difference between detected ions to identify ionization clusters, wherein similar ionization clusters are correlated to local damage to said condensed matter,
    wherein the pressure of the low-pressure gas is substantially equal to the pressure of gas in the ion detector.

2. The method of claim 1, wherein the condensed matter is selected from the group consisting of cells, polymers, nanoelectronics and nucleic acid molecules.

3. The method of claim 1 further comprising:
    determining effects of said ionizing radiation on said condensed matter by comparison of the identified ionization clusters to monte carlo simulations of ionizing radiation interactions with said condensed matter.

4. The method of claim 3, wherein said effects are selected from a DNA double strand break, a central nervous system effect, and cancer induction.

* * * * *